(12) United States Patent
Amirouche et al.

(10) Patent No.: US 9,883,834 B2
(45) Date of Patent: *Feb. 6, 2018

(54) MEDICATION DELIVERY DEVICE WITH MULTI-RESERVOIR CARTRIDGE SYSTEM AND RELATED METHODS OF USE

(76) Inventors: Farid Amirouche, Highland Park, IL (US); Matthew L. Cantwell, North Brook, IL (US)

( * ) Notice: Subject to any disclaimer, the term of this patent is extended or adjusted under 35 U.S.C. 154(b) by 786 days.

This patent is subject to a terminal disclaimer.

(21) Appl. No.: 13/448,013

(22) Filed: Apr. 16, 2012

(65) Prior Publication Data

US 2013/0274576 A1 Oct. 17, 2013

(51) Int. Cl.
*A61M 5/168* (2006.01)
*A61B 5/1455* (2006.01)
(Continued)

(52) U.S. Cl.
CPC .......... *A61B 5/4839* (2013.01); *A61B 5/0002* (2013.01); *A61B 5/14503* (2013.01); *A61B 5/14532* (2013.01); *A61M 5/1408* (2013.01); *A61M 5/1413* (2013.01); *A61M 5/14248* (2013.01); *A61M 5/1723* (2013.01); *A61B 5/6849* (2013.01); *A61B 2562/0295* (2013.01); *A61M 5/14224* (2013.01); *A61M 5/44* (2013.01); *A61M 5/445* (2013.01); *A61M 2205/3561* (2013.01); *A61M 2205/3569* (2013.01); *A61M 2205/3584* (2013.01); *A61M 2205/3592* (2013.01); *A61M 2205/36* (2013.01);
(Continued)

(58) Field of Classification Search
CPC .............. A61M 5/1408; A61M 5/1413; A61M 5/1723; A61M 5/14248; A61M 5/44; A61M 5/445; A61M 5/14224; A61M 2205/3561; A61B 5/14503; A61B 5/4839; A61B 5/6849
USPC ........... 604/65–67, 151, 180, 890.1; 600/365
See application file for complete search history.

(56) References Cited

U.S. PATENT DOCUMENTS 2,398,435 A 4/1946 Marks
3,137,242 A 6/1964 Hahn
(Continued)

FOREIGN PATENT DOCUMENTS

EP 0 024 431 B1 8/1985
EP 0 299 628 A1 1/1989
(Continued)

OTHER PUBLICATIONS

Anhalt et al., "Insulin Patch Pumps: Their Development and Future in Closed-Loop Systems, *Diabetes Technology & Therapeutics*," 2010, pp. 51-58, vol. 12.
(Continued)

*Primary Examiner* — Theodore Stigell
(74) *Attorney, Agent, or Firm* — Wilson Dutra, PLLC; Camille A. Wilson

(57) ABSTRACT

A medication delivery system for delivering medicament to a body of a user. The medication delivery system may include a housing having a plurality of medicament reservoirs therein, a first sensor configured to continuously monitor a parameter of the body, and a pump mechanism configured to pump medicament from each of the plurality of medicament reservoirs to a delivery mechanism having a portion disposed within the body of the user.

18 Claims, 15 Drawing Sheets

(51) Int. Cl.

| | |
|---|---|
| *A61M 5/142* | (2006.01) |
| *A61B 5/00* | (2006.01) |
| *A61B 5/145* | (2006.01) |
| *A61M 5/14* | (2006.01) |
| *A61M 5/172* | (2006.01) |
| *A61M 5/44* | (2006.01) |

(52) U.S. Cl.
CPC . *A61M 2205/3606* (2013.01); *A61M 2205/50* (2013.01); *A61M 2205/502* (2013.01); *A61M 2205/505* (2013.01); *A61M 2205/52* (2013.01); *A61M 2209/01* (2013.01); *A61M 2209/045* (2013.01); *A61M 2230/201* (2013.01)

(56) References Cited

U.S. PATENT DOCUMENTS

| | | |
|---|---|---|
| 3,498,228 A | 3/1970 | Blumle et al. |
| 3,691,263 A | 9/1972 | Stoy et al. |
| 3,771,694 A | 11/1973 | Kaminski |
| 3,827,565 A | 8/1974 | Matsumura |
| 3,889,710 A | 6/1975 | Brost |
| 3,915,609 A | 10/1975 | Robinson |
| 4,017,238 A | 4/1977 | Robinson |
| 4,197,266 A | 4/1980 | Clark et al. |
| 4,257,416 A | 3/1981 | Prager |
| 4,340,048 A | 7/1982 | Eckenhoff |
| 4,376,618 A | 3/1983 | Toyoda et al. |
| 4,415,003 A | 11/1983 | Paradis et al. |
| 4,498,843 A | 2/1985 | Schneider et al. |
| 4,544,369 A | 10/1985 | Skakoon et al. |
| 4,552,561 A | 11/1985 | Eckenhoff et al. |
| 4,657,486 A | 4/1987 | Stempfle et al. |
| 4,712,583 A | 12/1987 | Pelmulder et al. |
| 4,731,726 A | 3/1988 | Allen, III |
| 4,784,644 A | 11/1988 | Sawyer et al. |
| 4,797,144 A | 1/1989 | DeMeritt et al. |
| 4,840,754 A | 6/1989 | Brown et al. |
| 4,936,833 A | 6/1990 | Sams |
| 4,938,742 A | 7/1990 | Smits |
| 4,946,448 A | 8/1990 | Richmond |
| 4,947,856 A | 8/1990 | Beard |
| 4,958,661 A | 9/1990 | Holtermann et al. |
| 4,966,199 A | 10/1990 | Ruschke |
| 5,019,974 A | 5/1991 | Beckers |
| 5,050,612 A | 9/1991 | Matsumura |
| 5,147,323 A | 9/1992 | Haber et al. |
| 5,218,993 A | 6/1993 | Steinberg et al. |
| 5,246,634 A | 9/1993 | Ichikawa et al. |
| 5,370,635 A | 12/1994 | Strausak et al. |
| 5,584,815 A | 12/1996 | Pawelka et al. |
| 5,645,855 A | 7/1997 | Lorenz |
| 5,674,557 A | 10/1997 | Wildman et al. |
| 5,709,662 A | 1/1998 | Olive et al. |
| 5,762,632 A | 6/1998 | Whisson |
| 5,775,671 A | 7/1998 | Cote, Sr. |
| 5,822,715 A | 10/1998 | Worthington et al. |
| 5,858,001 A | 1/1999 | Tsals et al. |
| 6,003,736 A | 12/1999 | Ljunggren |
| 6,017,331 A | 1/2000 | Watts et al. |
| 6,056,716 A | 5/2000 | Funderburk et al. |
| 6,305,661 B1 | 10/2001 | Kennedy |
| 6,311,712 B1 | 11/2001 | Meyer |
| 6,315,929 B1 | 11/2001 | Ishihara et al. |
| 6,390,120 B1 | 5/2002 | Guala |
| 6,409,707 B1 | 6/2002 | Guala |
| 6,572,586 B1 | 6/2003 | Wojcik |
| 6,627,124 B1 | 9/2003 | Herbrechtsmeier et al. |
| 6,648,859 B2 | 11/2003 | Bitdinger et al. |
| 6,723,086 B2 | 4/2004 | Bassuk et al. |
| 6,813,906 B1 | 11/2004 | Hirota et al. |
| 6,945,963 B2 | 9/2005 | Langley et al. |
| 7,044,125 B2 | 5/2006 | Vedrine et al. |
| 7,081,108 B2 | 7/2006 | Langley et al. |
| 7,104,973 B2 | 9/2006 | Woolston et al. |
| 7,123,985 B2 | 10/2006 | Wildsmith et al. |
| 7,296,782 B2 | 11/2007 | Enerson et al. |
| 7,302,311 B2 | 11/2007 | Varis |
| 7,407,490 B2 | 8/2008 | Bendsen et al. |
| 7,470,266 B2 | 12/2008 | Massengale et al. |
| 7,510,544 B2 | 3/2009 | Vilks et al. |
| 7,537,590 B2 | 5/2009 | Santini, Jr. et al. |
| 7,585,167 B2 | 9/2009 | Lawton et al. |
| 7,637,899 B2 | 12/2009 | Woolston et al. |
| 7,846,146 B2 | 12/2010 | Woolston et al. |
| 7,850,663 B2 | 12/2010 | Sullivan et al. |
| 7,896,002 B2 | 3/2011 | Watanabe |
| 7,914,499 B2 | 3/2011 | Gonneili et al. |
| 7,935,280 B2 | 5/2011 | Lawton et al. |
| 7,967,795 B1 | 6/2011 | Cabiri |
| 8,021,334 B2 | 9/2011 | Shekalim |
| 8,771,229 B2 | 7/2014 | Amirouche et al. |
| 2002/0119711 A1* | 8/2002 | VanAntwerp et al. ....... 439/834 |
| 2003/0100883 A1 | 5/2003 | Kristensen et al. |
| 2003/0180164 A1 | 9/2003 | Bunner et al. |
| 2004/0050104 A1 | 3/2004 | Ghosh et al. |
| 2004/0176727 A1 | 9/2004 | Shekalim |
| 2005/0065500 A1 | 3/2005 | Couvillon et al. |
| 2005/0192557 A1* | 9/2005 | Brauker et al. ............... 604/503 |
| 2006/0021386 A1 | 2/2006 | Wang |
| 2006/0073232 A1 | 4/2006 | Wang |
| 2006/0145372 A1 | 7/2006 | Jones et al. |
| 2006/0224109 A1 | 10/2006 | Steil et al. |
| 2007/0073230 A1 | 3/2007 | Jasperson et al. |
| 2007/0087068 A1 | 4/2007 | Eiha et al. |
| 2007/0225147 A1 | 9/2007 | Hayashi et al. |
| 2007/0233008 A1 | 10/2007 | Kristensen et al. |
| 2007/0299398 A1* | 12/2007 | Alferness et al. ............ 604/151 |
| 2008/0169444 A1 | 7/2008 | Guala |
| 2009/0062767 A1 | 3/2009 | Van Antwerp et al. |
| 2009/0069650 A1 | 3/2009 | Jennewine |
| 2009/0105658 A1 | 4/2009 | Jennewine |
| 2010/0004603 A1 | 1/2010 | Kristensen et al. |
| 2010/0081993 A1 | 4/2010 | O'Connor |
| 2010/0100077 A1 | 4/2010 | Rush et al. |
| 2010/0185322 A1 | 7/2010 | Bylsma et al. |
| 2010/0225013 A1 | 9/2010 | Eiha et al. |
| 2010/0241086 A1 | 9/2010 | Yodfat et al. |
| 2010/0255366 A1 | 10/2010 | Myland |
| 2010/0256593 A1 | 10/2010 | Yodfat et al. |
| 2010/0280461 A1 | 11/2010 | Forstreuter |
| 2010/0317093 A1 | 12/2010 | Turewicz et al. |
| 2011/0021905 A1 | 1/2011 | Patrick et al. |
| 2011/0066131 A1 | 3/2011 | Cabiri |
| 2011/0114744 A1 | 5/2011 | Ricciardi et al. |
| 2011/0118675 A1 | 5/2011 | Miller et al. |
| 2011/0137287 A1 | 6/2011 | Gonnelli |
| 2011/0160696 A1 | 6/2011 | Hoss |
| 2011/0168294 A1 | 7/2011 | Jakobsen et al. |
| 2011/0251546 A1 | 10/2011 | Sullivan et al. |
| 2011/0274566 A1* | 11/2011 | Amirouche et al. .......... 417/322 |
| 2011/0308650 A1 | 12/2011 | Amirouche et al. |
| 2011/0309229 A1 | 12/2011 | Amirouche et al. |
| 2011/0309552 A1 | 12/2011 | Amirouche et al. |
| 2012/0002422 A1 | 1/2012 | Lia et al. |
| 2012/0053571 A1 | 3/2012 | Petri |
| 2013/0144214 A1 | 6/2013 | Amirouche et al. |
| 2013/0144254 A1 | 6/2013 | Amirouche et al. |
| 2013/0237947 A1 | 9/2013 | Amirouche et al. |
| 2013/0274577 A1 | 10/2013 | Amirouche et al. |
| 2013/0345650 A1 | 12/2013 | Amirouche |
| 2014/0155819 A1 | 6/2014 | Amirouche et al. |

FOREIGN PATENT DOCUMENTS

| | | |
|---|---|---|
| GB | 2 248 891 A | 4/1992 |
| JP | 62-297120 A | 12/1987 |
| JP | 2007-015906 A | 1/2007 |
| JP | 2007-0119280 A | 5/2007 |
| JP | 2008-96089 A | 4/2008 |
| WO | WO 03/047426 A1 | 6/2003 |
| WO | WO 2004/067964 A | 8/2004 |
| WO | WO 2006/111775 A | 10/2006 |
| WO | WO 2007/055642 A1 | 5/2007 |

(56) References Cited

FOREIGN PATENT DOCUMENTS

| WO | WO 2009/048462 | * | 4/2009 |
|---|---|---|---|
| WO | WO 2009/048462 A1 | | 4/2009 |
| WO | WO 2010/128914 A1 | | 11/2010 |

OTHER PUBLICATIONS

Einhorn et al., "Advances in Diabetes for the Millenium: Insulin Treatment and Glucose Monitoring," *Medscape General Medicine*, 2004, p. 8, vol. 6 (3 Suppl.).

Klonoff et al., "Insulin Pump Safety Meeting: Summary Report," *Journal of Diabetes Science and Technology*, 2009, pp. 396-402, vol. 3(2).

Elleri et al., "Closed-Loop Insulin Delivery for Treatment of Type 1 Diabetes," *BioMed Central*, 2011, p. 120, vol. 9.

Yadav et al., "Various Non-Injectable Delivery Systems for the Treatment of Diabetes Mellitus," *Endocrine, Metabolic & Immune Disorders—Drug Targets*, 2009, pp. 1-13, vol. 9(1).

Nisar et al., "MEMS-based Micropumps in Drug Delivery and Biomedical Applications," *Microsystem Technology*, 2008, pp. 917-942, vol. 130.

Amirouche et al., "Current Micropump Technologies and Their Biomedical Applications," *Microsystem Technology*, vol. 2009, pp. 647-666, vol. 15.

Roberts, "Blind Attack on Wireless Insulin Pumps Could Deliver Lethal Dose," Threatpost.com, Oct. 27, 2011.

Casella et al., "Accuracy and Precision of Low-Dose Insulin Administration," *Pediatrics*, 1993, pp. 1155-1157, vol. 29, No. 6.

Ignaut et al., "Comparative Device Assessments: Humalog KwikPen Compared with Vial and Syringe and FlexPen," 2009, pp. 396-402, vol. 3(2).

Meece et al., "Effect of Insulin Pen Devices on the Management of Diabetes Mellitus," *Am J Health-Syst Pharm*, 2008, pp. 1076-1082, vol. 65.

Bak et al., "Multiple Insulin Injections Using a Pen Injector Versus Insulin Pump Treatment in Young Diabetic Patients," *Diabetes Research*, 1987, pp. 155-158, vol. 6.

Selam, "Evolution of Diabetes Insulin Delivery Devices," *Journal of Diabetes Science and Technology*, 2012, pp. 505-513, vol. 4(3).

"Bartels micropumps," Apr. 2009, [online] http://www.bartelsmikrotechnik.de/index.php/micropumps.html.

"Diabetes Basics: Diabetes Statistics," American Diabetes Association, [Online]. Available at: http://www.diabetes.org/diabetes-basics/, [Accessed May 14, 2012] (3 pages).

"Diabetic Neuropathy, Living With Numbness and Pain," A Diabetic Life, [Online]. Available at: http://www.a-diabetic-life.com/diabetic-neuropathy.html. [Accessed May 5, 2012] (3 pages).

"Electromyogram (EMG)," MedicineNet.com, [Online]. Available at: http://www.medicinenet.com/electromyogram/article.htm. [Accessed May 15, 2012] (3 pages).

"Nerve conduction velocity," MedlinePlus®, A Service of the U.S. National Library of Medicine, National Institutes of Health, [Online]. Available at: http://www.nlm.nih.gov/medlineplus/ency/article/003927.htm; updated Jun. 18, 2011 (3 pages).

"Peripheral Neuropathy Fact Sheet," National Institute of Neurological Disorders and Stroke, NIH Publication No. 04-4853, [Online]. Available: http://www.ninds.nih.gov/disorders/peripheralneuropathy/detail_peripheralneuropathy.htm; updated Sep. 19, 2012 (9 pages).

"Peripheral Neuropathy Market Approaches US$1B by 2012," PR Newswire, United Business Media [Online]. Available at: http://www.prnewswire.co.uk/news-releases/peripheral-neuropathymarket-approaches-us1b-by-2012-154534705.html. Apr. 7, 2012 (2 pages).

"Silastic® BioMedical Grade ETR Elastomers", Dow Corning, 2002-2011, accessed at http://www4.dowcorning.com/DataFiles/090007c88028669a.pdf (5 pages).

"SILASTIC © Biomedical Grade Liquid Silicone Rubbers", Dow Corning, 2006, accessed at http://www4.dowcorning.com/DataFiles/090007c880097f96.pdf (6 pages).

"Small, powerful, light, precise: micro diaphragm pumps made of plastics: thinXXS micropumps" Mar. 2009, [online] http://www.thinxxs.com/main/produkte/micropumps.html (2 pages).

"Sylgard® 184 Silicone Elastomer", Dow Corning, 2007, accessed at http://ncnc.engineering.ucdavis.edu/pages/equipment/Sylgard_184_data_sheet.pdf (3 pages).

ACEVEDO, "Creation of Dual Chamber Micropump Using Rapid Prototyping," Milwaukee School of Engineering, Research Experience for Undergraduates Paper, 2005. Available online at: http://www.msoe.edu/academics/research_centers/reu/pdf/2005/Creation%20of%20a%20Dual%20Chamber%20Micropump%20using%20Rapid%20Prototyping.pdf (6 pages).

Barbano et al., "Effectiveness, Tolerabiiity, and Impact on Quality of Life of the 5% Lidocaine Patch in Diabetic Polyneuropathy," *Archives of Neurology*, 2004, pp. 914-918, vol. 61, No. 6.

Bohm et al., "A plastic micropump constructed with conventional techniques and materials," *Sensors and Actuators A*, vol. 77-3, pp. 223-228, 1999.

Dario et al., "A fluid handling system for a chemical microanalyzer," *J. Micromech. Microeng.*, vol. 6, pp. 95-98, 1996.

Davis et al., "Techniques for Improved Soft Lens Fitting"; Aug. 1, 2005, p. 2, accessed at http://www.clspectrum.com/articleviewer.aspx?articleid=12852 (5 pages).

Farnbach, "Peripheral Nerve Testing and Electromyography," [Online]. Available at: http://cal.vet.upenn.edu/projects/saortho/appendix_d/appd.htm. [Accessed May 18, 2012] (10 pages).

Fu et al. "TiNi-based thin films in MEMS applications: a review," *Sensors and Actuators A*, 2004, pp. 395-408, vol. 112, No. 23.

Galer et al., "The Lidocaine Patch 5% Effectively Treats All Neuropathic Pain Qualities: Results of a Randomized, Double-Blind, Vehicle-Controlled, 3-Week Efficacy Study with Use of the Neuropathic Pain Scale," *The Clinical Journal of Pain*, 2002, pp. 297-301, vol. 18, No. 5 (Abstract).

Gammaitoni et al., "Pharmacokinetics and Tolerability of Lidocaine Patch 5% with Extended Dosing," *The Annals of Pharmacotherapy*, 2002, pp. 236-240, vol. 36, No. 2, (Abstract).

Ha et al., "Disposable thermo-pneumatic micropump for bio lab-on-a-chip application," *Microelectronic Engineering*, 2009, pp. 1337-1339, vol. 86.

International Search Report and Written Opinion issued in International Patent Application No. PCT/US2009/059020, dated Mar. 9, 2010 (17 pages).

International Search Report and Written Opinion issued in International Patent Application No. PCT/US2012/066937, dated Mar. 7, 2013 (7 pages).

International Search Report and Written Opinion issued in International Patent Application No. PCT/US2013/035918, dated Jun. 21, 2013 (9 pages).

International Search Report and Written Opinion issued in International Patent Application No. PCT/US2013/035921, dated Jul. 1, 2013 (11 pages).

International Search Report and Written Opinion issued in International Patent Application No. PCT/US2013/046546, dated Aug. 8, 2013 (11 pages).

International Search Report and Written Opinion issued in International Patent Application No. PCT/US2013/072787, dated Apr. 24, 2014 (9 pages).

Irawan et al., "Fabrication and performance testing of disposable micropump suitable for microfluidic chip," in Intl. Conf. on Biomedical and Pharmaceutical Engineering, Orchard Hotel, Singapore, Dec. 2006, pp. 252-255.

Jeong, et al. "Fabrication of a peristaltic PDMS micropump," *Sensors and Actuators A*, vol. 123-124, pp. 453-458, 2005.

Junwu et al., "Design and test of a high-performance piezoelectric micropump for drug delivery," *Sensors and Actuators A*, vol. 121, pp, 156-161, 2005.

Koch, et al., "PDMS and tubing-based peristaltic micropumps with direct actuation," *Sensors and Actuators B*, vol. 135, pp. 664-670, 2009.

(56) References Cited

OTHER PUBLICATIONS

Laser et al., "A review of micropumps," J. Micromech. Microeng., vol. 14(6), pp. R35-R64, 2004.
Lee et al., "Microfluidic mixing: A review," Int. J. Mol. Sci., 2011, pp. 3263-3287, vol. 12.
Li et al., "A high frequency high flow rate piezoelectrically driven MEMS micropump" in Proceedings IEEE Solid State Sensors and Actuators Workshop, Hilton Head, SC, Jun. 2000 (4 pages).
Ma et al., "Development and application of a diaphragm micropump with piezoelectric device," Microsyst. Technol., vol. 14, pp. 1001-1007, 2008.
Manz et al., "Miniaturized total chemical analysis systems: a novel concept for chemical sensing," Sensors and Actuators B, vol. 1, pp. 244-248, 1990.
Melin et al., "A fast passive and planar liquid sample micromixer," Lab on a Chip, 2004, pp. 214-219, vol. 4.
Morrow, "Transdermal Patches are More Than Skin Deep," Managed Care [Online]. Available at: http://www.managedcaremag.com/archives/0404/0404.biotech.html. Apr. 2004 (4 pages).
Mundell, "Antidepressant Cymbalta Might Ease Chemo-Linked Pain," MSN Healthy Living, 2013 [Online]. Available at: http://health.msn.com/health-topics/cancer/antidepressant-cymbalta-might-ease-chemo-linked-pain (4 pages).
Nguyen et al., "MEMS-micropumps: a review," Journal of Fluids Engineering, vol. 124, p. 384-392, 2002.
Nguyen et al., "Microfluidics for Internal Flow Control: Micropumps," in *Fundamentals and Applications of Microfluidics*. Norwood, MA: Artech House, Inc., 2002; pp. 293-341.
Pallikaris, "Intracorneal mico-lens a minimally invasive option for presbyopia", Aug. 10, 2010, p. 1, paragraph 003, accessed at http://www.rigneygraphics.com/clients/presbia/website/newsmedia/pdfs/press-osn-presbia.pdf (2 pages).
Pan et el, "A magnetically driven PDMS micropump with ball check-valves," J. Micromech. Microeng, vol. 15, pp. 1021-1026, 2005.
Rapp et al., "Liga micropump for gases and liquids," Sensors and Actuators A, 1994, pp. 57-61, vol. 40, No. 1.
Richardson et al., "Peripheral Neuropathy: A True Risk Factor for Falls," The Journal of Gerontology: Series A, 1995, pp. 211-215, vol. 50, No. 4 (Abstract).
Rosielle, "The Lidocaine Patch," Medical College of Wisconsin [Online]. Available: http://www.eperc.mcw.edu/EPERC/FastFactsIndex/ff_148.htm. [Accessed May 15, 2012] (3 pages).
Santra et al., "Fabrication and testing of a magnetically actuated micropump," Sensors and Actuators B, vol. 87, pp. 358-364, 2002.
Shen et al., "Miniaturized PMMA ball-valve micropump with cylindrical electromagnetic actuator," Microelectronic Engineering, vol. 85, pp. 1104-1107, 2008.
Singhal, et al., "Microscale pumping technologies for microchannel cooling systems," Appl. Mech. Rev., vol. 57(3), pp. 191-221, 2004.
Star Micronics Co. Ltd., "Precision products," Mar. 2009, [online]. Accessed at: http://www.star-m.jp/eng/products/precision/index/html, on Aug. 22, 2011 (4 pages).
Trenkle et al., "Normally-closed peristaltic micropump with reusable actuator and disposable fluidic chip," Sensors and Actuators B, vol. 154, pp. 137-141, 2011.
Tsai et al., "Review of MEMS-based drug delivery and dosing systems," Sensors and Actuators A, vol. 134, No. 2, pp. 555-564, 2007.
U.S. Appl. No. 13/174,598, filed Jun. 30, 2011, by Amirouche et al.: Non-Final Rejection, dated May 14, 2013.
U.S. Appl. No. 13/174,598, filed Jun. 30, 2011, by Amirouche et al.: Final Rejection, dated Oct. 3, 2013.
U.S. Appl. No. 13/174,598, filed Jun. 30, 2011, by Amirouche et al.: Notice of Allowance, dated Apr. 7, 2014.
U.S. Appl. No. 13/174,624, filed Jun. 30, 2011 by Amirouche et al.: Non-Final Rejection, dated Jun. 28, 2012.
U.S. Appl. No. 13/174,624, filed Jun. 30, 2011 by Amirouche et al.: Final Rejection, dated Nov. 21, 2012.
U.S. Appl. No. 13/174,624, filed Jun. 30, 2011 by Amirouche et al.: Non-Final Rejection, dated Feb. 8, 2013.
U.S. Appl. No. 13/174,624, filed Jun. 30, 2011 by Amirouche et al.: Final Rejection, dated Jul. 31, 2013.
U.S. Appl. No. 13/174,624, filed Jun. 30, 2011 by Amirouche et al.: Notice of Allowance, dated Feb. 5, 2014.
U.S. Appl. No. 13/174,643, filed Jun. 30, 2011 by Amirouche et al.: Non-Final Rejection, dated May 2, 2013.
U.S. Appl. No. 13/174,643, filed Jun. 30, 2011 by Amirouche et al.: Notice of Allowance, dated Oct. 21, 2013.
U.S. Appl. No. 13/308,899, filed Dec. 1, 2011, by Amirouche et al.: Non-Final Rejection, dated Aug. 8, 2013.
U.S. Appl. No. 13/308,899, filed Dec. 1, 2011, by Amirouche et al.: Notice of Allowance, dated Feb. 28, 2014.
U.S. Appl. No. 13/370,091, filed Feb. 9, 2012, by Amirouche et al.: Non-Final Rejection, dated Aug. 21, 2013.
U.S. Appl. No. 13/370,091, filed Feb. 9, 2012, by Amirouche et al.: Notice of Allowance, dated Mar. 25, 2014.
U.S. Appl. No. 13/649,202, filed Oct. 11, 2012, by Amirouche: Non-Final Rejection, dated Jun. 18, 2013.
U.S. Appl. No. 13/649,202, filed Oct. 11, 2012, by Amirouche: Final Rejection, dated Jan. 15, 2014.
Van Lintel et al., "A piezoelectric micropump based on micromachining of silicon," Sensors and Actuators A, vol. 15, p. 153-167, 1988.
Yamahata et al. "A PMMA valveless micropump using electromagnetic actuation," Microfluid Nanofluid, vol. 1, pp. 197-207, 2005.
Zhu et al., "Optimization design of multi-material micropump using finite element method," Sensors and Actuators A, vol. 149, pp. 130-135, 2009.

* cited by examiner

MEDICATION DELIVERY DEVICE WITH MULTI-RESERVOIR CARTRIDGE SYSTEM AND RELATED METHODS OF USE

FIELD OF THE DISCLOSURE

Embodiments of the present disclosure relate to the field of medical devices and, in particular, to devices for delivery of medicament wirelessly and through programming. More specifically, embodiments of the present disclosure are directed to a wirelessly controlled medication delivery pump system that utilizes bidirectional communication and includes an external infusion device and a remote commander, a continuous glucose monitor, and an additional optional glucose monitor with a test strip on the controller.

BACKGROUND OF THE DISCLOSURE

Diabetes is a complex disease caused by the body's failure to produce adequate insulin or a cell's failure to respond to insulin, resulting in high levels of glucose in the blood. Type I diabetes is a form of diabetes mellitus that results from autoimmune destruction of insulin-producing beta cells of the pancreas in genetically predisposed individuals. There is no current cure, and treatment by injection or infusion of insulin must be continued indefinitely. Type II diabetes is a metabolic disorder brought on at any age by a combination of lifestyle, diet, obesity, and genetic factors. The World Health Organization recently revised its findings from a study conducted in 2004 with predictions that by 2030, 10% of the world's population of all ages will have either Type I or Type II diabetes. This translates to roughly 552 million people worldwide suffering from some form of this disease.

Typically, treatment for diabetes requires both repeated checking of blood glucose levels and several injections of insulin as prescribed by the physician throughout the day, since insulin cannot be taken orally. Major drawbacks of such treatment are the constant need to draw blood and test glucose levels throughout the day, improper or low dosage amounts of insulin, contamination of the insulin delivery system, lifestyle restriction, the unfortunate potential development of subcutaneous scar tissue due to repeated injections at the same location, and the high cost of medication, testing strips, and other treatment related materials.

Diabetes is usually controlled by insulin replacement therapy in which insulin is delivered to the diabetic person by injection to counteract elevated blood glucose levels. Recent therapies include the basal/bolus method of treatment in which a basal dose of a long-acting insulin medication, for example, Humalog® and Apidra®, is delivered via injection once every day, or, in the alternative, gradually throughout the day. The basal dose provides the body with an insulin profile that is relatively constant throughout the day, or could follow a profile best-suited for the particular diabetic patient. These rates can change based on the patient's response to insulin. At mealtime, an additional dose of insulin, or bolus, may be administered based on the amount of carbohydrate and protein in the meal. The bolus dose is viewed as an emergency response to spikes in blood sugar that need to be brought down by injection of insulin. Accurate calculations of various parameters, including, but not limited to, the amount of carbohydrates and proteins consumed, and the lapse in time since the last dosage are necessary to determine the appropriate dosage of insulin. The dosages are thus prone to human error and the method is ineffective when doses are skipped, forgotten, or miscalculated. Exercise, stress, and other factors can also cause the calculations to be inaccurate. Bolus doses are usually administered when the patient's glucose level is high or above certain acceptable thresholds and needs immediate attention.

To address these and other problems, insulin delivery devices or pumps were developed to mimic the way a normal, healthy pancreas delivers insulin to the body. Innovations are rapidly advancing toward the creation of a closed-loop insulin delivery system or "artificial pancreas." These systems employ real-time glucose-responsive insulin administration via continuous glucose monitoring and wireless communication with a controller which dispenses insulin based on tightly controlled algorithms. The two main algorithmic systems used to calculate insulin dosages automatically are the proportional-integral-derivative ("PID") control and the mathematic-predictive control ("MPC"). MPC algorithms can be considered proactive or predictive. They forecast glucose levels in anticipation of meals, physical activity and administer insulin over a prediction window of 1.5 to 3 hours or longer. PID algorithms, however, are considered reactive in response to measured glucose levels and cannot predict dosages. Unfortunately, there is currently no industry-wide standard in place for embedded algorithmic calculations, and dose calculations vary from device to device.

Often, both methods are utilized when insulin is coadministered with glucagon or other medication, although in computer simulations, glycemic regulation via MPC calculations may achieve superior glucose regulation. The future of this treatment protocol may depend on several factors: more accurate glucose sensors, rapid response software and hardware, single catheters for both glucose sensing and medication diffusion, and dual or multi-chambered medication delivery cartridge systems.

Recent innovations suggest that the addition of amylin analog hormone therapy, administered along with insulin and glucagon, delays glucose absorption and improves post-meal glucose control. Type 1 diabetics often lack counter-regulatory hormones like amylin, which is usually secreted with insulin in the healthy pancreas. The goal with diabetes treatment protocol is to achieve normoglycemia, or an HbA1c less than approximately 6.5%, a fasting glucose below approximately 100 mg/dL, postprandial glucose below approximately 140 mg/dL, and the avoidance of hypoglycemic excursions. Thus, the ability to deliver multiple medications simultaneously or independently would be highly desirable.

One recurring problem with most conventional miniaturized ambulatory infusion pumps is that the amount of medication which can be stored in the reservoirs often cannot meet the needs of certain diabetic patients. Many Type II diabetics who require insulin often need more insulin per gram of carbohydrate due to a condition referred to as "insulin resistance." Additionally, many diabetic therapies include one or more medications delivered alternately or simultaneously. For this reason, a medication pump which employs a plurality of reservoirs able to dispense medication at variable rates is highly desirable. Therefore, a substantial need exists to best maximize the volume of the medication reservoirs while maintaining a very small overall size of the device itself.

With the demand for a decrease in size of the pump unit also comes a decreased size in the medication reservoir. This reduced reservoir size means more frequent refilling, greater potential for contamination of the reservoir, more frequent changes of the cannula and tubing, and greater expense overall in treating the condition. Frequent manual refilling of a medication reservoir can also lead to the increased formation of bubbles, which is a significant problem. Even very small bubbles of 10 microliters or less can displace enough fluid to equal a missed dose of 1 unit of medicament. Insulin medication itself can also form bubbles when dissolved air is "outgassed" through normal changes in temperature or atmospheric pressure. Therefore the need exists to provide a disposable, prepressurized, prefilled medication reservoir that can work as part of a medication pump system to provide extremely accurate delivery of a plurality of medications.

SUMMARY OF THE DISCLOSURE

Embodiments of the present disclosure relate to the field of healthcare medical devices and, in particular, to devices for delivery of medicament wirelessly and through programming. More particularly, some embodiments provide systems and methods for a multiple drug delivery pump including independently actuating chambers using a disposable or refillable cartridge system. The cartridge system may be factory prefilled with insulin or other medicament in either one or two collapsible, elastomer reservoirs contained within a fully adaptable polymer microfluidic housing defining the flow control system, valve, micro channels and/or inlet/outlet units. The devices disclosed herein may be programmed or operated manually or independently of the remote controller using the pump unit attached to the body. In addition, the embodiments contemplated herein use a continuous body-parameter sensor in the pump unit and an independent glucose monitor on the handheld controller device.

In one embodiment, a medication delivery system for delivering a medicament to a body of a user may include a housing having a plurality of medicament reservoirs therein, a first sensor configured to continuously monitor a parameter of the body, and a pump mechanism configured to pump medicament from each of the plurality of medicament reservoirs to a delivery mechanism having a portion disposed within the body of the user.

Various embodiments of the medication delivery system may include one or more of the following features: the plurality of medicament reservoirs may include a first reservoir having a first medicament and a second reservoir having a second medicament; the first medicament may be fast-acting insulin, and the second medicament may be slow-acting insulin; the housing may include a height of approximately 0.5 inches; the parameter may be blood glucose; the first sensor may be removably secured to the housing, and the first sensor may include a cannula configured to be disposed within a user's blood stream; the plurality of reservoirs may be selectively removable from the housing; the housing may further include a display screen; the delivery mechanism may include an infusion set having a catheter; the pump mechanism may be configured to pump the first medicament at a first rate of delivery and the second medicament at a second rate of delivery; the pump mechanism may include at least one magnet and an electromagnetic coil; a second sensor configured to analyze a discrete sample for the parameter; both the first and second sensors may be integrated with the housing; the housing may further house electronics for controlling operation of the first sensor and the pump mechanism; the housing may include a plurality of surfaces, and at least one of the plurality of surfaces may include an adhesive material thereon; a handheld controller configured to communicate with the electronics within the housing; and the handheld controller may include a second sensor configured to analyze a discrete sample for the parameter.

In another embodiment, a pump mechanism for delivering a plurality of medicaments from a plurality of reservoirs, wherein the plurality of reservoirs are disposed within a housing configured to be secured to tissue of a user, may include a first pump insert body in fluid communication with a first reservoir of the plurality of reservoirs, a second pump insert body in fluid communication with a second reservoir of the plurality of reservoirs, wherein each of the first and second pump insert bodies includes a plurality of fluid channels, a fluid receiving opening, and a fluid discharge opening. The pump mechanism may also include a flexible member disposed in between the first and second pump insert bodies, wherein the flexible member may be operably coupled to first and second magnets. The pump mechanism may further include a plurality of electromagnetic coils configured to selectively attract one or both of the first and second magnets.

Various embodiments of the pump mechanism may include one or more of the following features: the plurality of reservoirs, the first and second pump insert bodies, and the flexible member may be disposed within a cartridge configured to be removably received in an opening of the housing; the plurality of reservoirs may include a first reservoir having a first medicament, and a second reservoir having a second medicament; the first medicament may be a fast-acting insulin, and the second medicament may be a slow-acting insulin; the housing may include a height of approximately 0.5 inches; the pump mechanism may be configured to be controlled by a handheld controller wirelessly coupled to the housing; the pump mechanism may be configured to pump the first medicament at a first rate of delivery and the second medicament at a second rate of delivery; the handheld controller may further include a sensor for analyzing a sample taken from a user's body; the sample may be blood; the housing may include a sensor module for continuously monitoring a parameter of the body of the user; and the sensor module may be removably coupled to the housing, and the parameter may be blood glucose.

A further embodiment of the present disclosure may include a medication delivery system for delivering a medicament to a body of a user. The medication delivery system may include a housing having first and second medicament reservoirs therein, a first sensor configured to continuously monitor a parameter of the body, and a pump mechanism configured to pump medicament from the first and second medicament reservoirs to a delivery mechanism. The pump mechanism may include a first pump insert body in fluid communication with a first reservoir of the plurality of reservoirs and a second pump insert body in fluid communication with a second reservoir of the plurality of reservoirs, wherein each of the first and second pump insert bodies includes a plurality of fluid channels, a fluid receiving opening, and a fluid discharge opening. The pump mechanism may also include a flexible member disposed in between the first and second pump insert bodies, wherein the flexible member is operably coupled to first and second magnets. The medication delivery system may further include a plurality of electromagnetic coils configured to selectively attract one or both of the first and second magnets.

Various embodiments of the medication delivery system may include one or more of the following features: the medicament in the first reservoir may be different from the medicament in the second reservoir; the medicament in the first reservoir may be a fast-acting insulin, and the medicament in the second reservoir may be a slow-acting insulin; the housing may include a height of approximately 0.5 inches; the parameter may be glucose; the first sensor may be removably secured to the housing, and wherein the first sensor may include a cannula configured to be disposed within a user's blood stream; the pump mechanism may be configured to pump the first medicament at a first rate of delivery and the second medicament at a second rate of delivery; a handheld controller wirelessly coupled to the housing, wherein the handheld controller may be discrete from the housing, and wherein the handheld controller may include a second sensor configured to analyze a discrete sample for the parameter; the housing may include a plurality of surfaces, and at least one of the plurality of surfaces may include an adhesive material thereon; the housing may include an actuator, and wherein selective actuation of the actuator causes the pump mechanism to pump a single dose of medicament from one of the first and second reservoirs for delivery to the user; and the first sensor is configured to be implanted within the body of the user, and wherein the first sensor is operably coupled to the housing via wireless communication.

Moreover, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

BRIEF DESCRIPTION OF THE DRAWINGS

The accompanying drawings illustrate certain exemplary embodiments of the present disclosure, and together with the description, serve to explain principles of the present disclosure.

DETAILED DESCRIPTION OF THE PREFERRED EMBODIMENTS

Figure 1A:
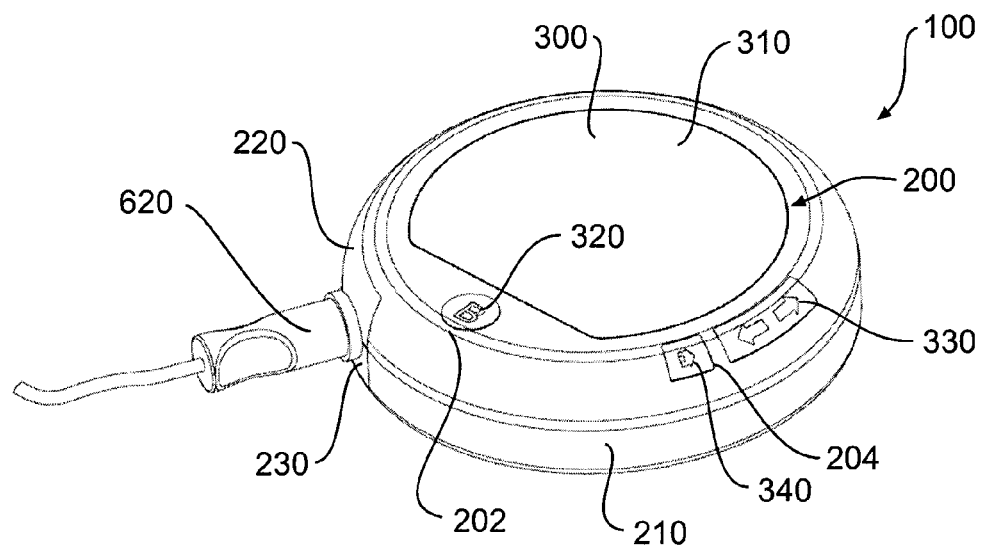
FIGS. 1A-1B depict perspective views an exemplary miniature medicament delivery and continuous monitoring system, in accordance with an embodiment of the present disclosure.

Reference will now be made in detail to the exemplary embodiments of the present disclosure described below and illustrated in the accompanying drawings. Wherever possible, the same reference numbers will be used throughout the drawings to refer to same or like parts.

Prior to providing a detailed description of the embodiments disclosed herein, however, the following overview is provided to generally describe the contemplated embodiments. Further, although the embodiments disclosed herein are described in connection with monitoring blood glucose, those of ordinary skill in the art will understand that the principles of the present disclosure may be suitable for monitoring any body parameter, including, e.g., blood pressure, cholesterol levels, sodium levels, medicament saturation levels, and so forth. Further, although the embodiments disclosed herein are described in connection with delivery of, e.g., insulin to treat diabetes, those of ordinary skill in the art will understand that any suitable therapeutic agent may be delivered to a patient, regardless of whether the agent is delivered to treat a disease state. For example, the embodiments disclosed herein may deliver medicaments for pain management, joint lubrication, or reverse controlled fluid extraction.

The disclosed embodiments relate to a miniature medicament delivery and, among other things, continuous glucose monitoring system. The term "fluid" may include a state of matter or substance (liquid or gas), whose particles can move about freely and has no fixed shape nor conforms to the shape of their containers. Further, the term "channel" may include a passage for fluids to flow through. Moreover, the term "medicament" may be used to refer to a substance used in therapy, a substance that treats, prevents, or alleviates the symptoms of disease, a medicine in a specified formulation, an agent that promotes recovery from injury or ailment, or any other fluid used in the treatment or diagnosis of a patient.

The embodiments described herein overcome at least certain disadvantages of the prior art by providing a multi-drug delivery device with a single cartridge system featuring multiple reservoirs. The reservoirs may be integrated to be actuated independently either manually or through the use of a remote commander with software encryption protection and multiple safety features. The cartridge system may be prefilled and disposable. In other embodiments, the cartridge system may be refilled by any suitable means.

The embodiments of the present disclosure rely on the data obtained from a continuous glucose metering and sensor device fully or partially imbedded in the user's body, and/or in conjunction with a manual test strip reader on the handheld controller/commander, to determine the basal and bolus insulin dosages for the user. In some instances, embodiments of the present disclosure may be configured to receive data that is obtained by a separate sensing device and then automatically or manually entered into the drug-delivery device or any associated component thereof. This data may then become part of the algorithm which automatically delivers the desired amount of medication into the user's body. The device may calculate the user's blood glucose level, and the result may be displayed on the screen of the device. In addition, any suitable means of communicating the user's blood glucose level to the user may be employed. Such means may include, but is not limited to, e.g., an audible announcement of calculated glucose level, a vibratory indication, and/or a tactile indication. If the glucose level is within range, then no action by the device is needed. If the glucose level is too high, however, or above the prescribed threshold, a bolus dose of insulin can be administered either by the user manually with the depression of the delivery button, or automatically by preprogramming the device. If the glucose level reading indicates that it is too low, the user can manually reduce the basal insulin dose or rate of delivery, or the device can be programmed to do this automatically. In addition to this function, a complete history of basal corrections and bolus delivery is stored in the device for use by the patient or by a healthcare provider for assessment and monitoring of the patient's healthcare. The stored history may be communicated, e.g., wirelessly, to a central database or the healthcare provider for evaluation.

More specifically, the present disclosure is drawn to a cartridge system having a plurality of collapsible reservoirs, each with a volume, preferably, of approximately 1.0 to 2.0 ml, with a more preferred volume of 1.5 ml. Each reservoir may interconnect in any combination to serve as complement to one another. Each of the plurality of reservoirs can be prefilled with similar or different medicaments. The basic mechanism of the drug delivery device is to actuate each fluid chamber and membrane individually, as described in greater detail below. The membrane of each individual actuation chamber may be placed between two suitable magnets, such as, e.g., gold-plated neodymium-iron-boron magnets (e.g., disk), that may be housed within each pump body insert. Each of the pump body cartridge inserts has a fluid receiving opening, a fluid discharge opening, a plurality of inlet channels, and a plurality of outlet channels. The pump body inserts may be placed between two inlet/outlet members. Each of the inlet/outlet members may have a fluid receiving opening, a fluid discharge opening, and a fluid outlet component. Additionally, each of the inlet/outlet members may include a male part that securely engages to a female part of the reservoir forming an airtight seal. The reservoir, the fluid receiving opening of the inlet/outlet member, the fluid receiving opening, the plurality of inlet channels, the plurality of outlet channels, and the fluid discharge opening of the pump body insert, the fluid discharge opening and the fluid outlet component of the inlet/outlet member may be in fluid communication. The cartridge system may further include valve membranes that are placed between the fluid receiving openings of the pump body inserts and the inlet/outlet members, and between the fluid discharge openings of the pump body inserts and the inlet/outlet members.

The valve membranes of the cartridge system can be an active valve magnetically operated and integrated into the membrane housing to control the opening and closing of the output flow. The feedback control allows for automatic opening or closing of the valve and dispersion of the medicament associated with the reservoir and the corresponding valve.

The present disclosure is also drawn to a cartridge system having one or more orifices to fill or refill a plurality of medicaments in the reservoirs. The one or more orifices may be located on the reservoirs, or on the inlet/outlet members, and the plurality of orifices are in fluid communication with the reservoirs.

The present disclosure is further drawn to a method of delivering medicament using a drug-delivery device having a cartridge system with multiple bilateral or parallel chambers. The method may include the steps of providing a drug delivery device having a multi-pump driver system and a cartridge system, loading a plurality of prefilled reservoirs containing fluid medicament into the cartridge system, engaging securely with the cartridge system and the pump driver system, selecting various parameters on a user interface of the pump driver system, including selecting predetermined values or specifying user-defined values for the parameters, and connecting suitable delivery mechanisms, such as, e.g., an infusion set, to the drug delivery device.

With the aid of an optional single reservoir, continuous medication flow can be achieved. The two collapsible reservoirs are permanently adhered to the valve covers creating an air-tight seal, and separated within the housing by a thin polymer shield. The cartridge is part of a magnetic medication pump mechanism and, hence, contains the dynamic flow control channels and valves, as well as the magnets that are an integral part of the design, as discussed below. As a result, the plurality of reservoirs may remain permanently sterile and impervious to outside contaminants. The medication delivery pump assembly of the present disclosure may be worn outside the body, and the medication may be dispensed into the body via an attachable infusion set, which may be connected to a suitable outlet. Embodiments of the present disclosure further contemplate using a far-field radio frequency communication system to integrate the pump with a hand-held remote control device. Those of ordinary skill will recognize that any suitable wired or wireless (e.g., infrared, Bluetooth, Wi-Fi, etc.) means of communication may be used. The drug delivery system or pump may further include a digital remote controller that wirelessly communicates with the pump control unit, operating and controlling the delivery of the drug through the interface of a cartridge.

The method of delivering medicament using the drug delivery device disclosed herein may include the additional steps of placing an infusion set on a body part of a patient, attaching the infusion set to the patient's body, attaching the infusion set to the pump outlets and commencing drug delivery from the drug delivery device. Although the embodiments of the present disclosure describe an exemplary infusion set, any suitable mechanism for delivering medicaments to a patient's body may be used.

The method of delivering medicament using the drug delivery device described herein may further include the step of connecting an infusion set to the drug delivery device. The method may also include the steps of connecting one end of a Y-catheter, or more than one Y-catheters to an outlet component of an inlet/outlet member, and delivering each fluid medicament at a given rate. The step of delivering fluid medicament at a given rate can further include delivering fluid medicament at a controlled and continuous rate for a predetermined or user-defined period of time. Alternatively, the step of delivering fluid medicament at a given rate can further include delivering fluid medicament at a programmable rate that is regulated by the patient.

The present disclosure also contemplates a method of delivering medicament using the drug delivery device having a cartridge system. The method may include the steps of providing a drug delivery device having a pump driver system and a cartridge system, loading a plurality of reservoirs to the cartridge system, using an instrument to inject a plurality of fluid medicaments into the plurality of reservoirs, engaging the cartridge system securely to the pump driver system, selecting various parameters on a user interface of the pump driver system including selecting predetermined values or specifying user-defined values for the parameters, and connecting an infusion set to the drug delivery device. The step of connecting an infusion set to the drug delivery device may further include the steps of connecting one end of a Y-catheter to an outlet component of an inlet/outlet member and delivering fluid medicament at a given rate. The step of delivering fluid medicament at a given rate can further include delivering fluid medicament at a controlled and continuous rate for a predetermined or user-defined period of time. Alternatively, the step of delivering fluid medicament at a given rate can further include delivering fluid medicament at a programmable rate that is regulated by the patient.

The present disclosure further contemplates a drug delivery device having a pump driver system, a cartridge system, a cannula and an insertion mechanism, and a plurality of conduits. The pump driver system may include a driver that drives the magnets that apply forces to the pump membranes of the cartridge system, a controller in communication with the pump to adjust the force applied by the driver, a power source, and a user interface configured to present information to a user. The cartridge system of the device may snap (or otherwise frictionally engage) into the pump drivers of the pump system and is securely engaged to it. Each of the plurality of conduits may include a proximal end, a distal end, and a lumen extending from its proximal end to its distal end. The proximal ends of the plurality of conduits may be securely engaged to the distal ends of the cannula and the insertion mechanism, and the distal ends may be securely engaged to the proximal ends of the fluid outlet component of the inlet/outlet members of the cartridge system.

As alluded to above, the embodiments of the present disclosure relate to miniature medicament delivery and continuous monitoring systems, and, more particularly, to miniature insulin electromagnetic micropumps and continuous glucose monitoring systems. The electromagnetic micropumps disclosed herein may be useful for, e.g., delivering insulin to diabetic patients, and also may be used for delivering other drugs to any desired patient. The continuous glucose monitoring module disclosed here is useful for determining the level of glucose in a patient's body in a continuous manner. Those of ordinary skill will recognize that the continuous monitoring embodiments disclosed herein may be useful for monitoring any desired body parameter, not just blood glucose.

Referring now to the drawings, FIGS. 1A-1E illustrate a medicament delivery and continuous monitoring system 100, in accordance with an embodiment of the present disclosure. The medicament delivery and continuous monitoring system 100 may include an upper housing 200, a lower housing 210, an upper cartridge housing 220, a lower cartridge housing 230, an adhesive patch platform 240, a screen 300, a screen cover 310, a bolus button 320, a navigation button 330, a home button 340, a continuous monitoring sensor body 400, a continuous monitoring cannula 420, a continuous monitoring support socket 430, a continuous monitoring sensor release button 450, a plurality of continuous monitoring sensor release button springs (not shown), a plurality of continuous monitoring sensor release leaf springs (not shown), a plurality of clamshells (not shown), a plurality of pump insert bodies (not shown), a plurality of inlet/outlet members (not shown), a plurality of electromagnetic coils 560, a pump membrane (not shown), a plurality of permanent magnets (not shown), a plurality of prestressed membranes (not shown), a plurality of reservoirs (not shown), a catheter 620, a circuit board (not shown), and a plurality of batteries (not shown).

In one embodiment, the medicament delivery and continuous monitoring system 100 may be affixed directly to the skin via adhesive patch platform 240. Adhesive patch platform 240 may include any suitable hypoallergenic adhesive material capable of affixing system 100 to the skin of a user. In some embodiments, the adhesive material may be reusable. In other embodiments, the system 100 may be carried or worn by a user. For example, the system may be carried in a pocket of a clothing article, worn around a patient's neck, or may be worn on an arm or leg band.

The disclosed system may have any suitable configuration desired. For example, as shown in FIG. 1A, the system may have a substantially circular configuration, which does not include any sharp edges, thereby allowing the system to be worn discretely beneath a patient's clothing. In other embodiments, such as, e.g., shown in FIGS. 2A-2C, the disclosed system may have a substantially rectangular configuration. Regardless of the specific configuration chosen, the system of the present disclosure may have a substantially low-profile (e.g., slim profile) configuration. That is, the height of the disclosed system 100 may be selected to allow a user to wear the system 100 close to the skin and discreetly beneath clothing. In some embodiments, the height of system 100 may be in the range of approximately 0.25 inches to 1.5 inches, with a preferred height of approximately 0.5 inches or less.

As noted above, system 100 may include an upper housing 200 and lower housing 210. Upper and lower housings 200, 210 may be fabricated from any suitable process known in the art. For example, housings 200, 210 may be made from extrusion or molding. Further, housings 200, 210 may be made from any suitable materials. Such materials may include, but are not limited to, plastics, thermoplastics, and/or elastomers. One suitable material may be Acrylonitrile butadiene styrene (ABS) or equivalents. Housings 200, 210 may be provided with any suitable coating desired. For example, housings 200, 210 may be coated with, e.g., hypoallergenic agents to reduce discomfort to a patient's skin. Further, one or more of housings 200, 210 may be provided with a fragrant coating that may please or soothe a user. Instead of a coating, such agents may be impregnated within one or more external walls of housings 200, 210. Furthermore, housings 200, 210 may be provided in any suitable color or color combination. The housings 200, 210 may be configured to form a hermetic sealed when operably coupled. In addition, as will be discussed in greater detail below, housings 200, 210 may be provided with one or more storage locations. Such storage locations may be secured or unsecured. Moreover, cartridge 230, discussed greater below, may be of a different color than one or both of housings 200, 210, and cartridge 230 may be capable of illumination to indicate use or dispensing of medicaments contained therein.

Figure 1B:
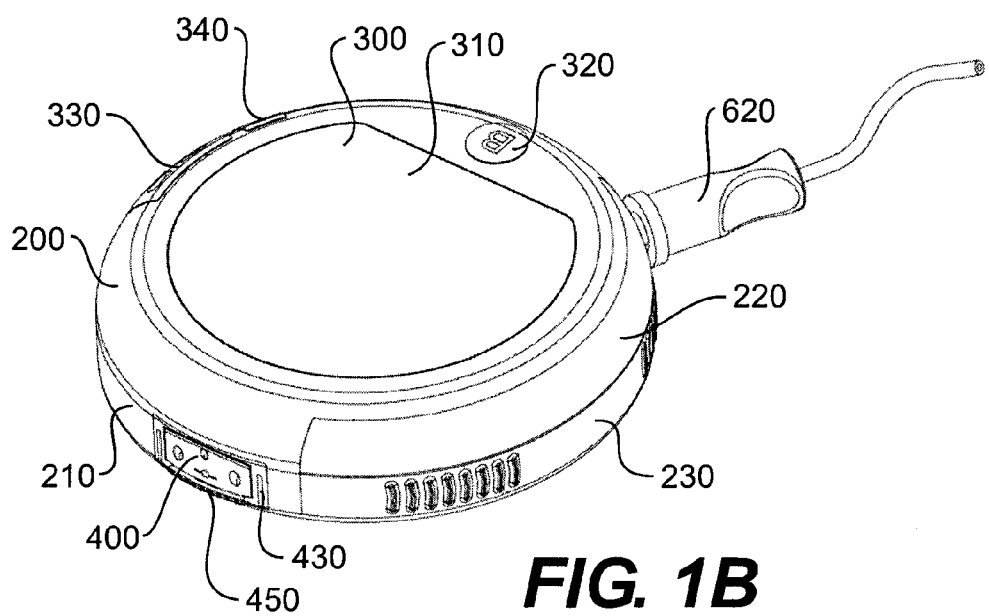

With specific reference to FIGS. 1A-1B, system 100 may include a screen 300 for, e.g., displaying one or more system parameters (e.g., battery life), the time and date, monitored body parameters, date and time of last dose, and any other information that may be communicated to a user of system 100. Screen 300 may be any suitable screen known in the art. For example, screen 300 may be a Liquid Crystal Display (LCD) or an Organic Light Emitting Diode (OLED) display capable of black-and-white or colored graphics. Further, screen 300 may be configured as a "touch-screen," permitting a user to control one or more functions of system 100 by touching various portions of the screen. In this manner, the user may operate or program system 100 by accessing one or more menus through direct interaction with screen 300. Screen 300 may be provided a screen cover 310 or with any suitable coating. Such coatings may protect screen 300 from, e.g., scratches or other damage. In addition, the applied coatings may reduce glare, permitting a user to effectively view the contents of screen 300 in daylight during outdoor activities. Further, screen 300 may be provided with a privacy coating, permitting view of the screen contents at only a predetermined angle of viewing.

An operator of system 100 may also control system 100 via one or more buttons, such as, e.g., buttons 320, 330, and 340. Buttons 320, 330, and 340 may be any suitable button interface known in the art. For example, buttons 320, 330, and 340 may include push buttons, slide buttons, and/or touch buttons that may be activated without any relative movement between the buttons and associated housing. Buttons 320, 330, and 340 may be located on any suitable surface of a housing (e.g., upper and/or lower housings 200, 210) of system 100. Although the depicted embodiment includes three buttons, those of ordinary skill in the art will recognize that any suitable number of buttons may be included. Further, the buttons 320, 330, and 340 may be disposed separately from one another or grouped together as desired. One or more buttons 320, 330, and 340 may be multifunctional. That is, a single button may be capable of executing a plurality of functions. For example, various portions of the same button may be configured to execute differing functions. In addition, depressing a particular button for a short time may execute a first function, while pressing and holding the same button in the depressed location may be execute a second function.

With specific reference to FIG. 1A, bolus button 320 may be disposed on upper housing 200. Bolus button may be linked with suitable electronics to effect delivery of a bolus drug dose. Further, button 330 may be a multifunctional button. Particularly, button 330 may allow a user to navigate one or more menus or select between a plurality of options to effectively operate system 100. As such, button 330 may be capable of multiple functions by, e.g., depressing a first portion of button 330 to perform a first function and depressing a second portion of button 330 to perform a second function. Further, system 100 may be provided with a "home" button 340, which may be configured to allow a user to clear a selection or to return to a main menu. Home button 340 may be also configured to power on and off system 100, by, e.g., pressing and holding button 340.

System 100 may also include at least one outlet mechanism for delivering medicaments to a patient. In the present disclosure, the outlet mechanism is exemplified by a conventional infusion set known in the art. However, any suitable outlet mechanism may be used. The described infusion set may include a catheter 620 having a proximal end, a distal end, and a suitable length therebetween. A proximal end of the catheter may be operably coupled to system 100 and one or more reservoirs therein, and a distal end of catheter 620 may be operably coupled to a thin, flexible needle suitable for long term placement into a patient's skin. Catheter 620 may have any suitable configuration and shape, and may be flexible to permit relief of stresses imposed on catheter 620 by, e.g., a patient's movements.

In some embodiments, system 100 may be configured to regulate the temperature of the contents of reservoirs 600, 610. For example, system 100 may include miniature, portable chillers and/or heaters for maintaining the requisite temperatures of certain medicaments.

Figure 1C:
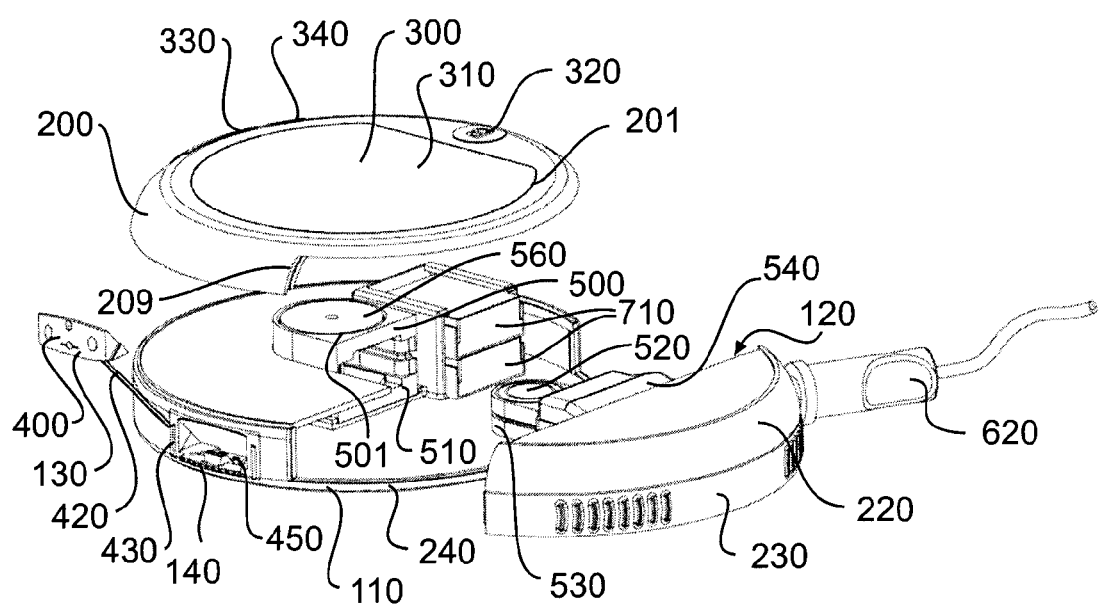
FIG. 1C depicts an exploded view of the exemplary miniature medicament delivery and continuous monitoring system of FIGS. 1A-1B.
Figure 1D:
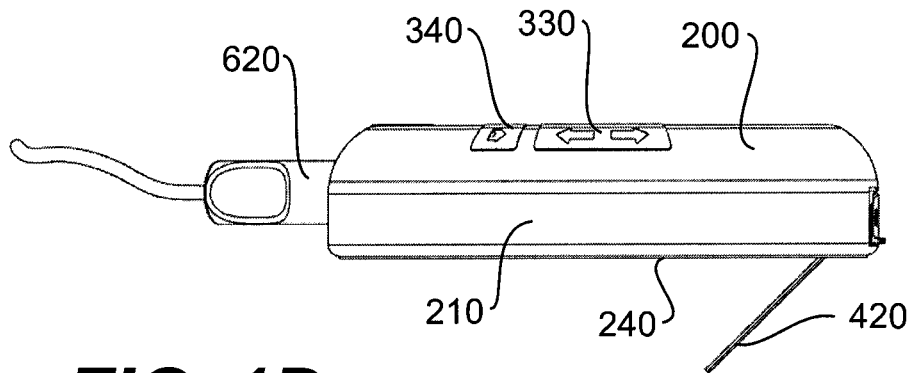
FIGS. 1D-1E depict side elevation views of exemplary miniature medicament delivery and continuous monitoring system of FIGS. 1A-1B.
Figure 1E:
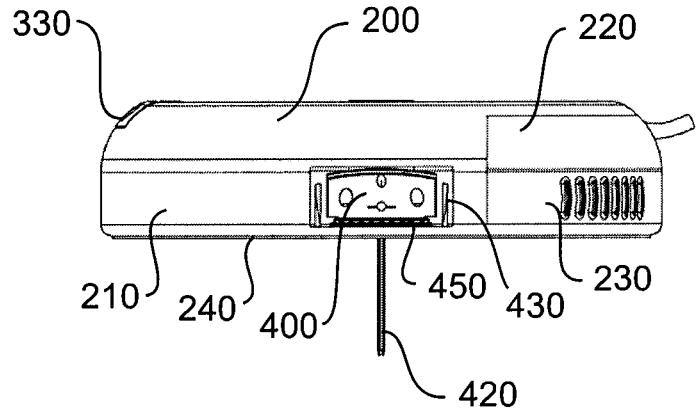

FIG. 1C shows an exploded view of medicament delivery and continuous monitoring system 100, showing the base subassembly 110, the cartridge system 120, the continuous monitoring sensor module 130, the continuous monitoring support module 140.

As alluded to above, and with reference to FIG. 6B, depressing bolus button 320 triggers the micropump (described below in greater detail) to deliver as many bolus doses as required by the patient. The micropump assembly includes a first pump insert body 520, a second pump insert body 530, a flexible membrane 570 disposed therebetween, four prestressed membranes 590 designed and positioned in order to prevent fluid backflow, two magnets 580 attached to flexible membrane 570 and two electromagnetic coils 560 (shown in FIG. 1C), which may be made of copper or any other suitable material. The first pump insert body 520 and second pump insert body 530 may be secured in between a first clamshell 500 and a second clamshell 510, as shown in FIG. 1C. A first inlet/outlet member 540 (FIGS. 6B and 8A-8B) may provide a fluidic link between a first reservoir 600 and the first pump insert body 520 and between the first pump insert body 520 and the catheter 620, which delivers the medicament to the patient. A second inlet/outlet member 550 provides a fluidic link between a second reservoir 610 and the second pump insert body 530 and between the second pump insert body 530 and the catheter 620.

With renewed reference to FIG. 1C, the system 100 may include a sensor support module 140 for operably coupling with a sensor 130. In one embodiment, the sensor 130 may be configured to continuously monitor the blood glucose of a patient. However, those of ordinary skill will understand that the principles of the present disclosure contemplate using any suitable sensor for monitoring any body parameter. Nonetheless, and solely for purposes of efficiency, the description hereon will be directed to a sensor for continuously monitoring glucose levels within a patient. However, any suitable body parameter may be monitored.

With specific reference to FIGS. 1C, 1E, 4, 5A, and 5B, attached to the continuous glucose monitoring sensor body 400 may be a continuous glucose monitoring cannula 420, the in vivo portion that is configured to be inserted at, e.g., a 45° angle into the subcutaneous tissue of the diabetic patient. The angle of insertion is merely exemplary, and any suitable of angle of insertion, including, e.g., 90° may be employed within the principles of the present disclosure. The sensor body 400 may be any suitable housing containing relevant electronics of the sensor module 130. Sensor body 400 may be received and housed in continuous glucose monitoring support socket 430 attached to, e.g., lower housing 210. Sensor body 400 may be released from its support socket upon pressing continuous glucose monitoring release button 450, which unloads continuous glucose monitoring leaf springs 470 and pushes sensor body 400 outward. Release button 450 goes back to its normal position via a plurality of continuous glucose monitoring release button springs 460.

Sensor 130 may be any suitable sensor known in the art capable of continuously monitoring a body parameter over extended periods of time. In one embodiment, sensor 130 may monitor a patient's blood glucose. To that end, cannula 420 may be configured to penetrate a patient's skin for placement within a patient's blood stream for extended periods of time. Thus, it is contemplated that cannula 420 may be relatively flexible and include relatively small dimensions. Cannula 420 may also include any suitable coating desired. For example, cannula 420 may be coated with anticoagulation and/or antibiotic agents. Further, sensor 130 may sense a patient's blood glucose by any known sensing technologies, including, but not limited to, technologies employing chemical and/or optical sensing technologies.

Control electronics may be provided on a circuit board within system 100 for controlling the micropump assembly, the continuous glucose monitoring module, and the display to screen 300. A wireless module (not shown) may relay data between the medicament delivery and continuous glucose monitoring system 100 and a remote controller. An embodiment of the disclosed device may be powered by a pair of batteries 710 (FIG. 1C) secured to lower housing 210. Batteries 710 may be any suitable batteries known in the art. In some embodiments, batteries 710 may be single-use batteries, which may require periodic replacement. In other embodiments batteries 710 may be batteries that may be selectively rechargeable. In such instances, batteries 710 may be removed from system 100 and placed into suitable recharging apparatus until power is fully restored. In even further embodiments, batteries 710 may be configured to be recharged without requiring removal from within system 100. For example, such batteries 710 may be recharged wirelessly without removal from system 100.

Figure 1F:
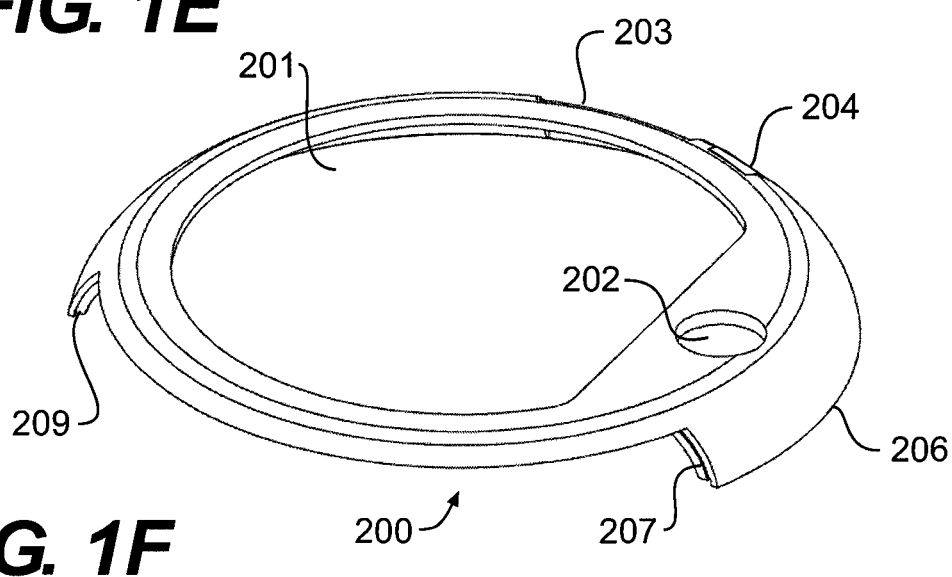
FIG. 1F depicts an upper component of a housing of the exemplary miniature medicament delivery and continuous monitoring system of FIGS. 1A-1B.
Figure 3:
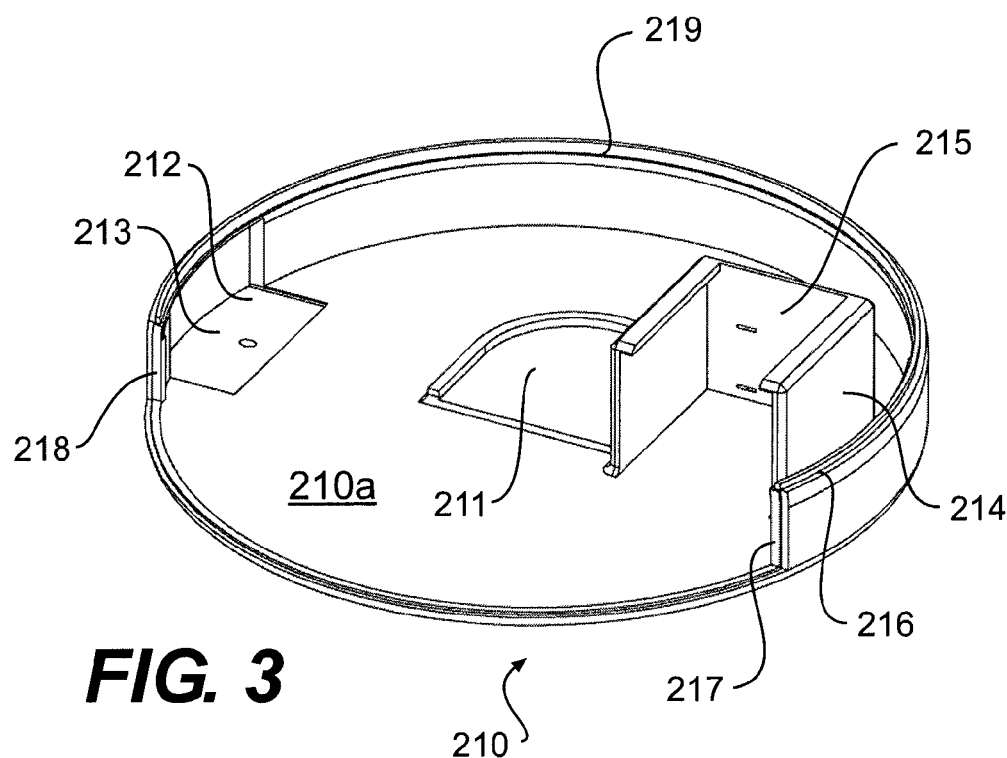
FIG. 3 depicts a housing component of the exemplary miniature medicament delivery and continuous monitoring system of FIGS. 1A-1B.

Referring to FIGS. 1F and 3, the upper housing 200 shows an opening 201 designed to house screen 300 and screen cover 310, and a plurality of openings 202, 203, 204 designed to house bolus button 320, directional button 330, and home button 340. An inner groove 206 is designed to align with the inner lip 216 of lower housing 210 shown in FIG. 3, and an inner lip 207 is designed to align with the inner groove 227 of upper cartridge housing 220 shown in FIGS. 6A-6B. A circuit board may be aligned and secured between inner groove 209 of upper housing 200 and inner groove 219 of lower housing 210.

Referring now to FIG. 3, lower housing 210 may include an exemplary diameter of about 2.20 inches. Lower housing 210 may further include an insert 211 designed to receive, support, and/or frictionally support a lower clamshell 510 (shown in FIG. 1C). An insert 212 on the side of the housing with aperture 213 is designed to position the continuous glucose monitoring support socket 430 and let the continuous glucose monitoring cannula 420 get through the housing. A protruding holder 214 is designed to align and secure the plurality of batteries 710 that are stopped in the sliding direction by wall 215. An inner lip 217 is designed to align with the inner groove 237 of lower cartridge housing 230 shown in FIGS. 10A-10B. The lower housing 210 may further include a plurality of lateral locking grooves 218 that clip onto deformable locking hooks 238 of the lower cartridge housing 230 when the cartridge is inserted into the system. In addition, those of ordinary skill in the art will recognize that any suitable means of securing the cartridge housing 230 to lower housing 210 may be utilized within the principles of the present disclosure.

One or both of housings 200, 210 may include a storage cavity. The storage cavity may be configured to store any suitable items. For example, the storage cavity may store medicine pills, needles, and/or glucose test strips. The cavity may be secured by, e.g., a door.

Figure 2A:
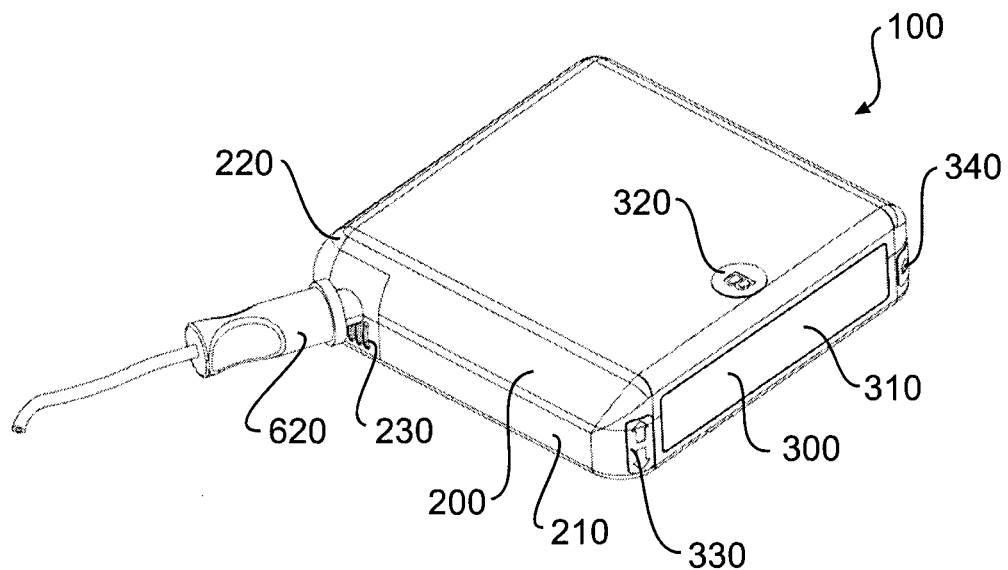
FIGS. 2A-2B depict perspective views of an exemplary miniature medicament delivery and continuous monitoring system, in accordance with another embodiment of the present disclosure.
Figure 2B:
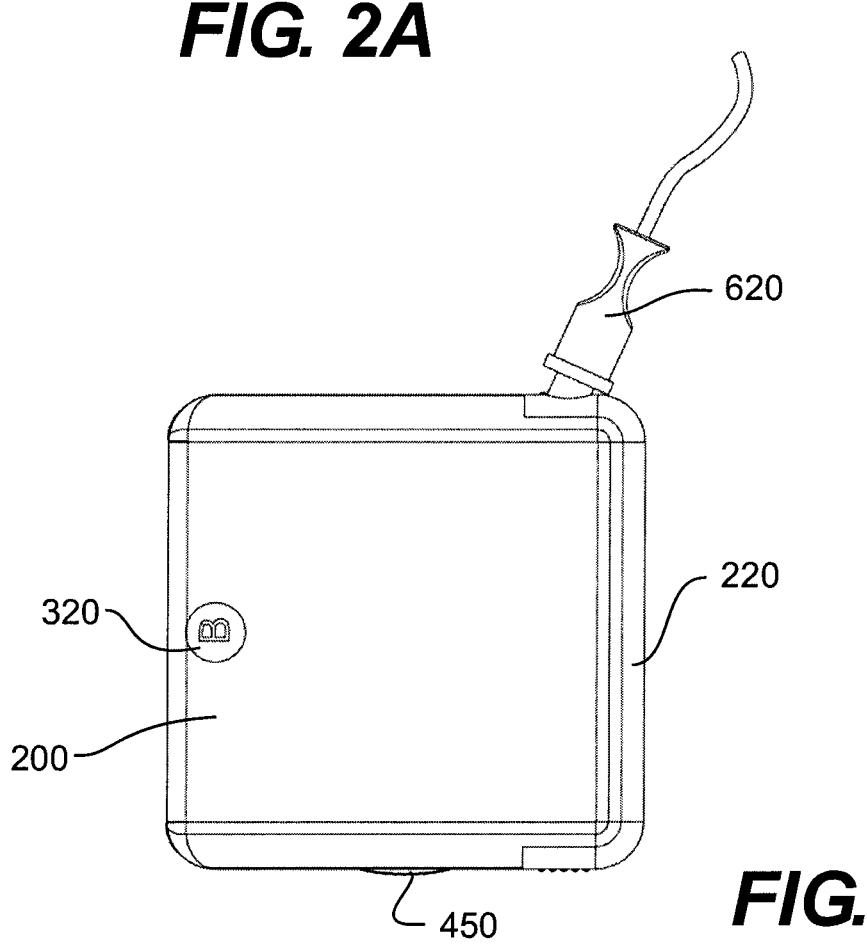
Figure 2C:
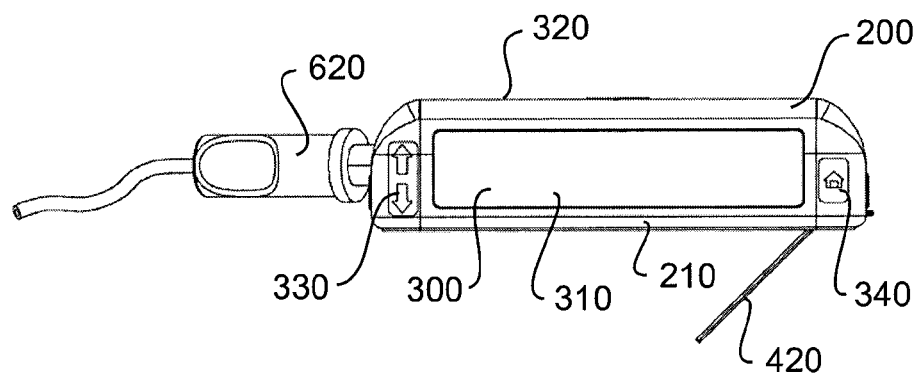
FIG. 2C illustrates a side elevation view of the exemplary miniature medicament delivery and continuous monitoring system of FIGS. 2A-2B.

As alluded to above, system may have any suitable shape and/or configuration. With reference to FIGS. 2A-2C, system 100 may include a rectangular shape. In such an embodiment, buttons 320, 330, and 340 may be disposed at any suitable location on housings 200, 210. For example, as shown, bolus button 320 may be disposed on a side of system 100 that is different than the side that buttons 330 and 340 are disposed on. Further, screen 300 may be disposed on a side of that allows a user to view the contents of screen 300 with relative ease.

Figure 4:
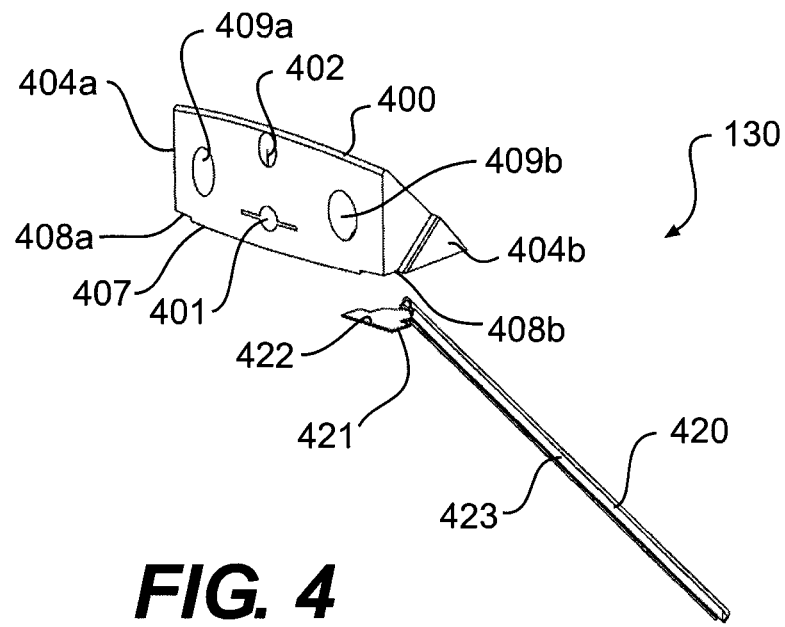
FIG. 4 illustrates an exemplary sensor module for continuously monitoring a body parameter.
Figure 5A:
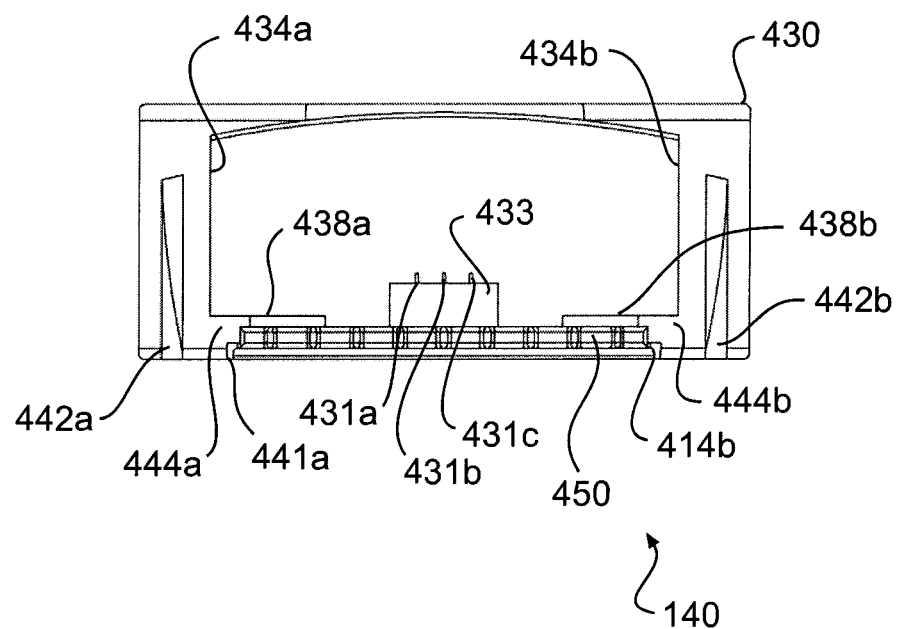
FIGS. 5A-5B depict various views of an exemplary support module for receiving the sensor module of FIG. 4.
Figure 5B:
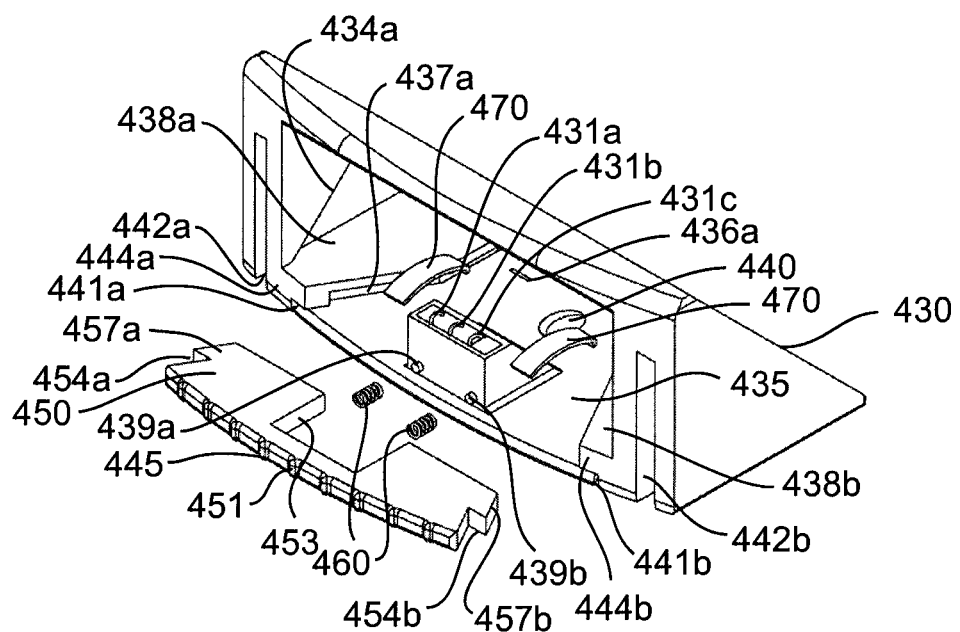

Referring now to FIGS. 4 and 5A-5B, the continuous glucose monitoring sensor module 130 and support module 140 are shown. Continuous glucose monitoring sensor body 400 has an aperture 401 designed to house continuous glucose monitoring cannula 420. After mounting cannula 420 onto sensor body 400, aperture 401 may be filled with waterproof glue to ensure cannula 420 is efficiently isolated from the external environment. In addition, any suitable means for securing and isolating cannula 420 may be used. Aperture 402 of sensor body 400 is designed to temporarily lodge a hard insertion needle (not shown) protecting cannula 420 during its insertion into the patient's body, and aperture 440 of support socket 430 is designed to let the continuous glucose monitoring cannula 420 get through the socket. The insertion needle may be attached to a plunger (not shown) presenting a plurality of cylindrical protrusions that stick into a plurality of apertures 409a, 409b making a 45° angle with mating surface 405 during the insertion of cannula 420 into the patient's body. The insertion of cannula 420 into the patient's body is concurrent with the insertion of sensor body 400 into support socket 430 via the plunger/needle mechanism. Sensor body 400 has a recess (not shown) that ensures the electrical contacting area 421 of continuous glucose monitoring cannula 420 is accessible and can make contact with a plurality of flexible electrical contacts 431a, 431b, 431c on protrusion 433 of support socket 430. The support socket 430 may be designed to house electrical wires (not shown) linking the continuous glucose monitoring cannula 420 and the control electronics on a circuit board within system 100. A plurality of cuts 441a, 441b, 442a, 442b on the bottom surface of support socket 430 allow part of the support socket to deform sideways in a symmetric manner during the 45° angle insertion of sensor body 400 into support socket 430 due to a plurality of wedge-shaped protrusions 404a, 404b on the sides of sensor body 400. Protrusions 404a, 404b ultimately snap behind a plurality of abutments 434a, 434b of support socket 430 after local strain release in the support socket, in order to ensure the locking of sensor body 400 onto support socket 430. Mating surface 405 comes in contact with mating surface 435 of support socket 430 and mating surfaces 408a, 408b come in contact with mating surfaces 438a, 438b of support socket 430 after sensor body insertion. The continuous glucose monitoring sensor body 400 is preferably made of clear acrylic. However, any suitable biocompatible material may be used. The in vivo portion 423 of cannula 420 is approximately 0.80 inch long.

The continuous glucose monitoring sensor module 130 may be changed every three to seven days due to the progressive wearing of the glucose oxidase. In order to remove this subassembly from the continuous glucose monitoring support module 140 and the rest of the medicament delivery and continuous glucose monitoring system 100, a user may press continuous glucose monitoring release button 450 via a plurality of grip protrusions 451. Release button 450 is spring-loaded by a plurality of release button springs 460 positioned by a plurality of cylindrical bumps 439a, 439b on protrusion 433 on one side and a plurality of cavities 459a, 459b on recess 453 of release button 450 on the other side. Mating surface 455 of release button 450 is in contact with mating surface 435, recess 407 of sensor body 400 is designed to lodge release button 450, and a plurality of recesses 454a, 454b are in contact with a plurality of abutments 444a, 444b of support socket 430 and designed to snap release button 450 into support socket 430. Depressing button 450 causes slanted ramps 457a, 457b to come in contact with slanted cuts 437a, 437b of support socket 430, which causes part of support socket 430 to deform laterally and abutments 434a, 434b to move away from one another. The angle slanted ramps 457a, 457b and slanted cuts 437a, 437b make with release button 450 push direction is preferably about 30°. When protrusions 404a, 404b totally clear abutments 434a, 434b during the depression of release button 450, a plurality of compressed leaf springs 470 inserted in cuts 436a, 436b of support socket 430 release their potential energy and exert a force on surfaces 406a, 406b of sensor body 400 that consequently comes slightly out of its socket 430. The patient may then pull off the continuous glucose monitoring sensor module 130 completely.

Although the disclosed embodiments illustrate a continuous monitoring module physically connected to housings 200, 210 of system 100, those of ordinary skill will appreciate that any suitable mechanism of continuously monitoring a body parameter may be used within the principles of the present disclosure. For example, a fully implantable sensor module (not shown) may be implanted within a patient's body for extended periods of time. Such a module may be self-contained and self-sustaining. For example, the implantable module may include electronics, algorithms, and other components necessary to detecting the body-parameter (e.g., glucose) and communicating it to system 100 wirelessly. For example, the implantable module may be a small chip or self-contained electronics module. To that end, the implantable module may include a long-lasting power source, or a power source that may recharged wirelessly by, e.g., remote power conduction or induction.

Figure 6A:
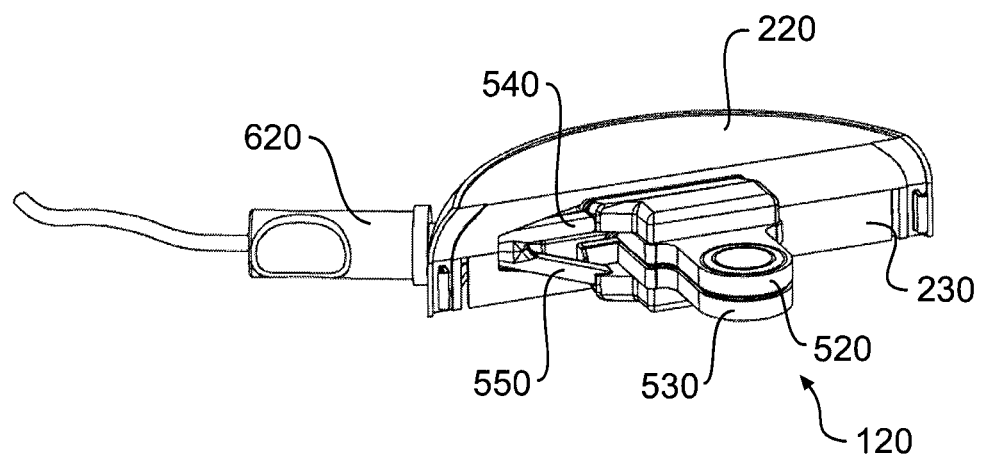
FIGS. 6A-6B depict perspective and exploded views of an exemplary cartridge assembly for use with the exemplary miniature medicament delivery and continuous monitoring system of FIGS. 1A-1B, in accordance with an embodiment of the present disclosure.
Figure 6B:
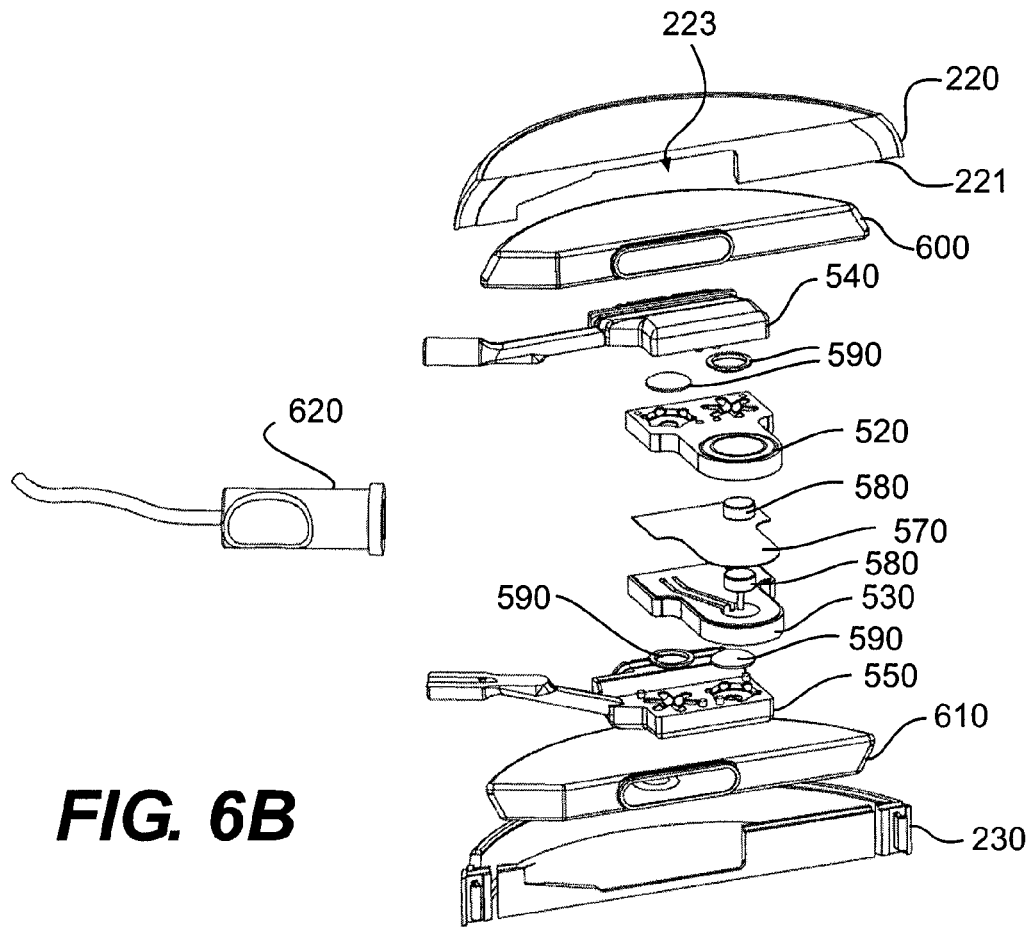

Referring now to FIGS. 6A-6B, the cartridge system 120 may be composed of pump insert bodies 520, 530, flexible membrane 570, magnets 580, prestressed membranes 590, inlet/outlet members 540, 550, reservoirs 600, 610, upper and lower cartridge housings 220, 230, and catheter 620. Cartridge system 120 may include any suitable shape and/or configuration. For example, as shown in FIGS. 6A-6B, cartridge system 120 may be configured to correspond to a portion of the circular configuration of system 100. In addition, cartridge system 120 may include any suitable number of reservoirs and associated dispensing components.

For example, although the depicted embodiment illustrates two reservoirs, cartridge system 120 may include a greater or lesser number of reservoirs. In one exemplary embodiment, cartridge system 120 may include four or six reservoirs and associated dispensing components. Moreover, cartridge system 120 may be configured for replacement and disposal after a single use. In such an embodiment, the reservoir(s) of cartridge system 120 may be prefilled by a manufacturer and provided to a user of system 100 for insertion into system 100. In other embodiments, the reservoir(s) of cartridge system 120 may be selectively refillable with desired medicaments. Still further, cartridge system 120 may be configured to provide an indication to a user of the level of contents with the reservoirs of cartridge system 120. For example, upper and lower cartridge housings 220, 230 may have transparent portions that may allow a user to visually inspect the remaining contents through a corresponding transparent portion in reservoirs 600, 610. In other embodiments, upper and lower cartridge housings 220, 230 may have a suitable gauge that communicates the level of contents in reservoirs 600, 610 as detected by a suitable sensing mechanism placed within reservoirs 600, 610.

Reservoirs 600, 610 may be any suitable container for storing and dispensing suitable medicaments or agents. In one embodiment, the contents of reservoirs 600, 610 may be delivered to a patient by a suitable pump mechanism, as discussed in greater detail below. In other embodiments, reservoir 600, 610 may be self-emptying reservoirs. To this end, one or more walls of each of reservoirs 600, 610 may be made of an elastic material, which may apply a force to the contents within reservoirs 600, 610.

With renewed references to FIG. 1C, a first clamshell 500 having an opening 501 for an electromagnetic coil 560 is shown. The first clamshell 500 may include an aperture designed to house the first pump insert body 520. The first pump insert body 520 may rest on a thin peripheral layer of preferred thickness of approximately 0.005 inches, which may be configured to constrain the distance between electromagnetic coil 560 and pump insert body 520 to its given thickness. The clamshell 500 may further include flanges or any other suitable geometric features designed to facilitate a smooth and preferable insertion of the cartridge system 120 into the clamshells 500, 510. The second clamshell 510 is substantially symmetrical in geometry to the first clamshell 500. The clamshells 500, 510 may be made of polyvinyl chloride (PVC) or any suitable material known in the art.

Figure 7A:
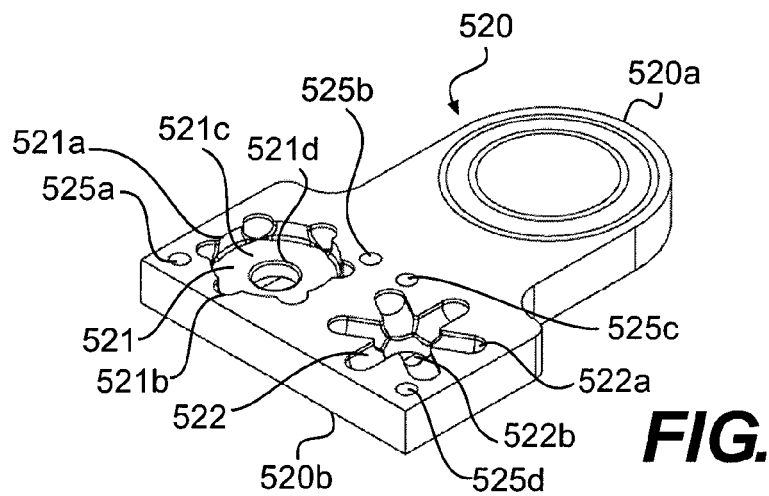
FIGS. 7A-7C depict various views of a pump insert body for use with the exemplary miniature medicament delivery and continuous monitoring system of FIGS. 1A-1B.
Figure 7B:
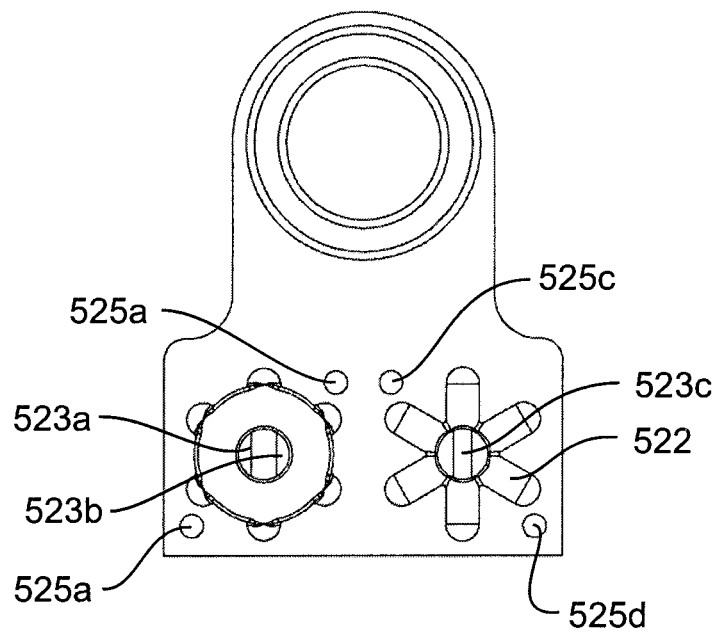
Figure 7C:
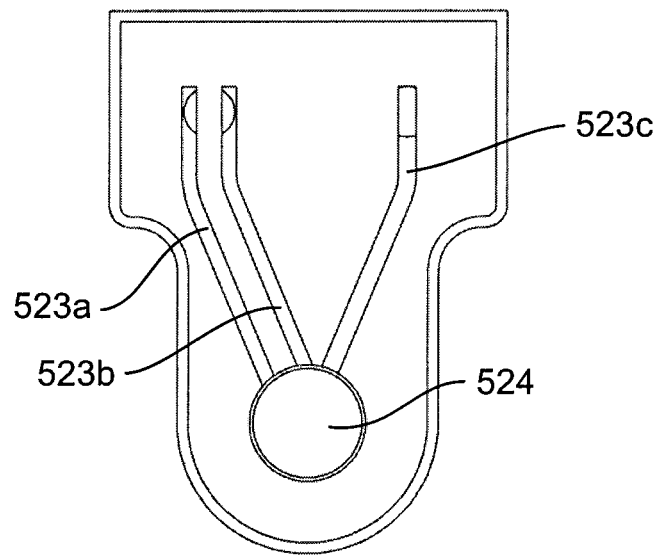

Focusing now on FIGS. 7A-7C, a first insert body 520, having fluid receiving 521, and discharge 522, openings is shown. Initially, those of ordinary skill in the art will recognize that although first insert body 520 includes a substantial planar configuration, any suitable configuration may be used within the principles of the present disclosure. Pump insert body 520 may include an elongate member having a first curved end 520a and a second straight end 520b disposed opposite the curved end. The second, straight end 520b may include a length larger than a diameter of the first curved end 520a. The fluid receiving and discharge openings 521, 522 may be disposed adjacent the second, straight end 520b.

As shown in FIG. 7A, fluid receiving opening 521 may be substantially circular. However, any suitable shape and configuration may be employed within the principles of the present disclosure. Fluid receiving opening 521 may include a substantially circular periphery 521 having a plurality of semi-circular notches 521b therein. Although the depicted embodiments include six semi-circular notches 521b, circular periphery 521 may include a greater or lesser number of notches 521b. In addition, the configuration of any particular notch 521 may differ relative to the configurations of other notches 521b. Fluid receiving opening 521 may further include a base 521c having an opening 521d therein. Opening 521 may also be substantially circular. However, a diameter of opening 521d may be less than that of periphery 521.

Fluid discharge opening 522 may include a substantially "flower-shaped" configuration. As shown in FIG. 7A, opening 522 may include a plurality of petals 522a disposed about a central opening 522b. Although the depicted embodiment illustrates six petals 522a, any suitable number of petals 522a may be provided. In addition, as shown, opening 522b may be recessed relative to petals 522a. Further, although the depicted embodiment illustrates each of petals 522a having a substantially similar configuration, those of ordinary skill will recognize that each of petals 522a may have a differing configuration relative to the other of petals 522a.

The first insert body 520 also includes a plurality of fluid channels 523a, 523b, 523c, for instance, two input channels 523a, 523b, and one output channel 523c. However, those of ordinary skill in the art will recognize that any suitable number of fluid channels may be provided. Further, fluid channels 523a, 523b, 523c may include any suitable shapes and/or configurations. For example, each of fluid channels 523a, 523b, 523c may include a substantially circular cross-section configuration. Moreover, the cross-sectional configurations of one of fluid channels 523a, 523b, 523c may vary relative to the other of fluid channels 523a, 523b, 523c. Even further, the cross-sectional configuration of one of fluid channels 523a, 523b, 523c may vary along its length. In some embodiments, one or more of fluid channels 523a, 523b, 523c may be provided with a suitable metering mechanism for controlling the flow of fluids through fluid channels 523a, 523b, 523c.

The plurality of fluid channels 523a, 523b, 523c may be in fluid communication with the receiving and discharge openings 521, 522, respectively. The plurality of fluid channels 523a, 523b, 523c may be designed to provide membrane support thereby preventing deformation and reverse flow of fluids. The first pump insert body 520 may include an opening 524 to house a magnet 580 (FIG. 6B). Although magnet 580 is depicted as a disk, magnet 580 may include any suitable shape, structure, and configuration. Apertures 525a, 525b, 525c, 525d may be used to align and/or secure the first pump insert body 520 to the first inlet/outlet member 540 via protrusions 545a, 545b, 545c, 545d, shown in FIGS. 8A-8B.

The second pump insert body 530 may be substantially symmetrical in geometry to the first pump insert body 520. The first and second pump bodies 520, 530 may be made of any suitable material, including, but not limited to, clear acrylic.

The cartridge system 120 may further include a pump membrane 570 as shown in FIG. 6B. The pump membrane 570 may be a biocompatible elastomer membrane, preferably made of Silastic Q7-4840 and of preferable thickness of approximately 0.005 inches. The pump membrane 570 may be placed between two disk magnets 580, which are housed within a plurality of openings 524, 534 of the first and second pump insert bodies 520, 530, as shown in FIG. 6B. The disk magnets may include gold-plated neodymium-iron-boron grade N42 magnets. However, any suitable magnets may be used. The volume of fluid medicaments in the cartridge system may be related to the diameter of the magnets 580 and the stroke length. The stroke length can be electromagnetically controlled and monitored by a driver feedback system.

Figure 8A:
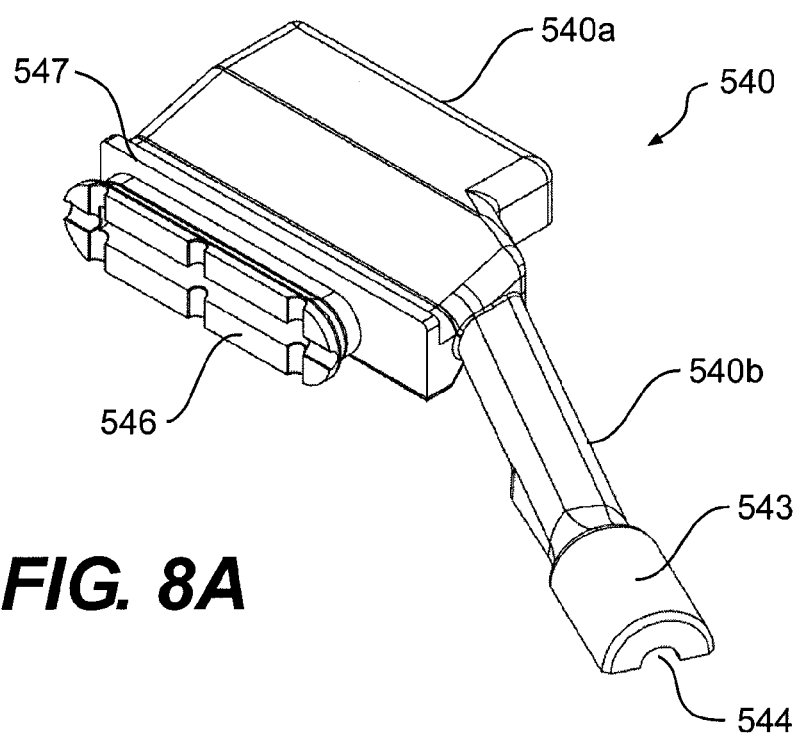
FIGS. 8A-8B depict various views of an inlet/outlet member for use with the exemplary miniature medicament delivery and continuous monitoring system of FIGS. 1A-1B.
Figure 8B:
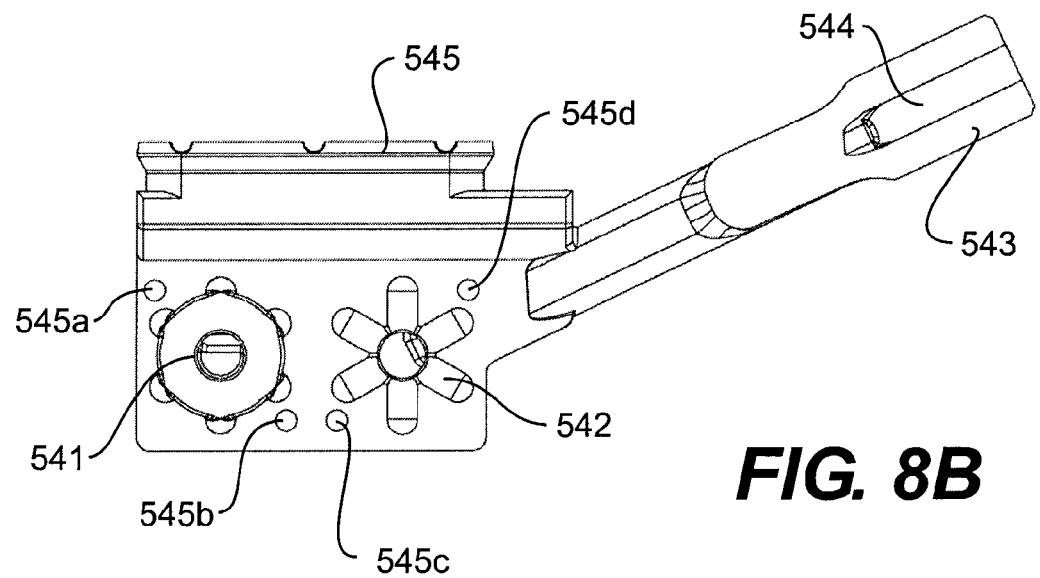

Referring now to FIGS. 8A-8B, a first inlet/outlet member 540 having fluid receiving 541, and discharge 542, openings is shown. The inlet/outlet member 540 has a fluid outlet component 543 having a semi-cylindrical body which contains an outlet channel 544 that operably connected with the fluid discharge opening 542 for receiving fluid medicament. The semi-cylindrical fluid outlet component 543 of first inlet/outlet member 540 may be operably connected to fluid outlet component 553 of second inlet/outlet member 550 to form a cylindrical fluid outlet component that is attached to the fluid inlet component of catheter 620, which ultimately directs the medicament to a user's body. As a result of fluid outlet component 543 being fluidly coupled to fluid outlet component 553, the principles of the present disclosure provide for discharging a plurality of medicaments through a single delivery mechanism connected to the patient. To this end, the principles of the present disclosure delivery medicaments that require reconstitution just prior to delivery to a patient.

Figure 9:
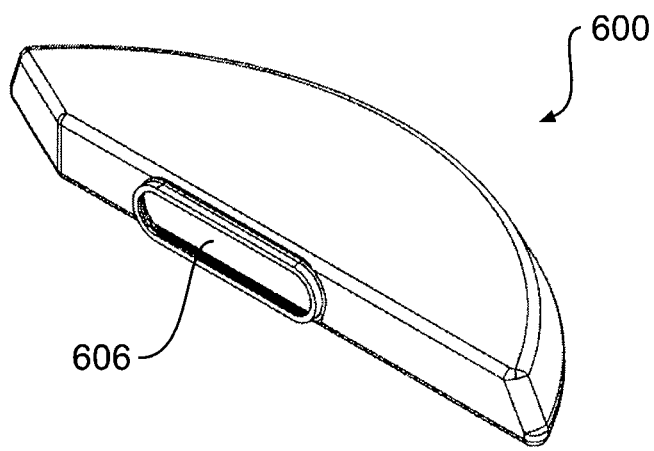
FIG. 9 shows a perspective view of a reservoir, in accordance with an embodiment of the present disclosure.

The inlet/outlet member 540 may include a male part 546 that is configured to engage female part 606 of the first reservoir 600 shown in, e.g., FIG. 9. In alternate embodiments, e.g., inlet/outlet member 540 may include a female part that is configured to be operably connected with a male part extending from reservoir 600. The male part 546 of inlet/outlet member 540 can have tooth-like channels to ensure that a low resistance path for fluid flow exists for all configurations of the reservoirs 600, 610. Protrusions 545a, 545b, 545c, 545d may be used to align and/or secure the first inlet/outlet member 540 to the first pump insert body 520. Protrusion 547, inserted in lip 224 of upper cartridge housing 220, may designed to position (e.g., orient) and secure the first inlet/outlet member 540 in the cartridge.

As shown in FIG. 8, first inlet/outlet member 540 may comprise of base portion 540a and extension 540b. Base portion 540a may include any desirable configuration for fluidly communicating with pump insert bodies 520. In addition, extension 540b may be configured to channel medicament from base portion 540a to catheter 620.

The second inlet/outlet member 550 may substantially symmetrical in geometry to the first inlet/outlet member 540. Inlet/outlet members 540, 550 are preferably made of clear acrylic. However, any suitable material may be used. Moreover, although the figures illustrate only two inlet/outlet members, the principles of present disclosure contemplate any suitable number of inlet/outlet members that correspond to the number of reservoirs in system 100.

Turning now to FIG. 9, a reservoir 600 having an opening 606 is shown. The reservoir 600 may be made of elastomers and preferably made by liquid injection molding of Silastic Q7-4840 or transfer molding of Medical Grade Polyisoprene. However, any suitable method of manufacture and material may be used. The polymer reservoirs allow better use of the interior volume available within the cartridge body, and the collapsible nature of the material allows for more innovative methods for withdrawing the liquid contents. The second reservoir 610 is substantially symmetrical in geometry to the first reservoir 600.

As alluded to above, reservoirs 600, 610 may be self-emptying in some embodiments. To this end, reservoirs 600, 610 may include optional mechanisms for applying a force to an exterior wall of reservoirs 600, 610. For example, reservoirs 600, 610 may include leaf or Belleville springs secured to an external wall. In other embodiments, one or more walls of reservoirs 600, 610 may be elastic or spring-like in nature. Further, in some embodiments, reservoir 600 may contain a medicament that is different from the one contained within reservoir 610. For example, reservoir 600 may contain a fast-acting insulin and reservoir 610 may contain a slow-acting insulin. In addition, reservoirs 600, 610 may contain differing ingredients, which, when mixed together, combine to form a particular medicament within the patient's body. With regard to volume, reservoir 600, 610 may collectively provide a total medicament volume of approximately 302 ml or units.

Figure 10A:
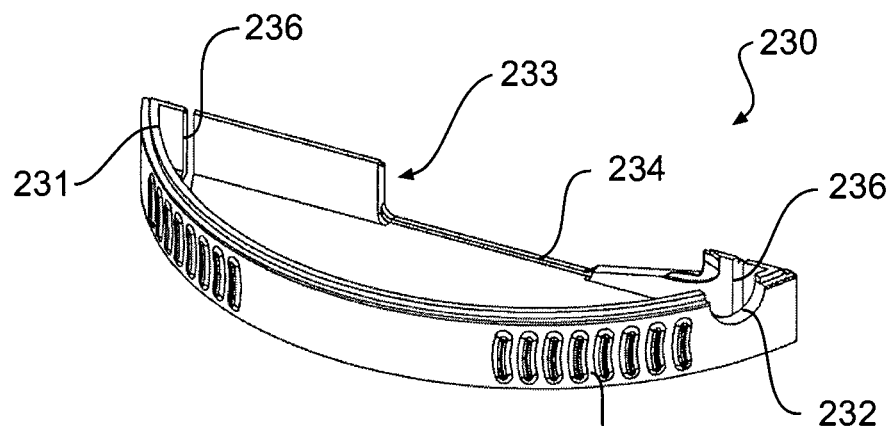
FIGS. 10A-10B depict various views of a reservoir cartridge housing for use with the exemplary miniature medicament delivery and continuous monitoring system of FIGS. 1A-1B.
Figure 10B:
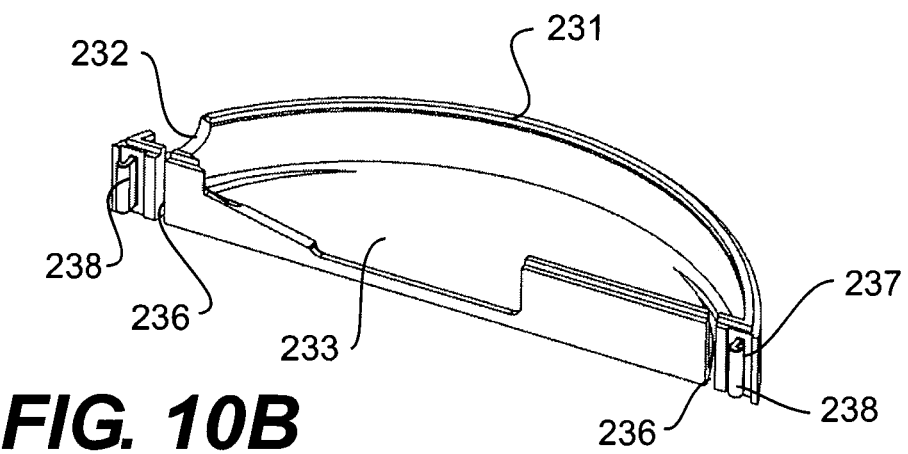

Turning now to FIG. 6B, the upper cartridge housing 220 has an inner groove 221 designed to align with inner lip 231 of lower cartridge housing 230 (FIGS. 10A-10B). The upper cartridge housing 220 may include an aperture (not shown) corresponding to aperture 232 of lower housing 230 to let outlet components 543, 553 of inlet/outlet members 540, 550 get through the cartridge housings 220, 230, so that catheter 620 may be attached to the cartridge system 120. An aperture 223 is designed to cooperate with aperture 233 of lower cartridge housing 230 to let the majority of inlet/outlet members 540, 550 get through the cartridge housings 220, 230.

Turning now to FIGS. 10A and 10B, the lower cartridge housing 230 may include grip protrusions 235 that release locking hooks 238 of lower cartridge housing 230 from locking groove 218 of lower housing 210 whenever pressed by the user due to the local deformation of the cartridge housing made possible by cuts 236, allowing one to remove the cartridge system 120 and to access batteries 710. However, any suitable mechanism for retaining and releasing cartridge system 120 to and from lower housing 210 may be employed. The cartridge housings 220, 230 may be of, e.g., of ABS.

With reference to FIGS. 1C, 6A-10B, an exemplary pumping operation will be described. As alluded to above, the disclosed system is capable of delivering a plurality of medicaments at differing delivery rates. For example, a basal dose may include a constant delivery of a small dose of, e.g., insulin. On the other hand, a bolus dose may include large dose selectively delivered to the patient, as desired. While the below description will reference a bolus delivery, the operation of the pumping mechanism disclosed herein will be substantially the same for basal deliveries.

System 100 may receive instructions for a bolus event by one of a number of ways. For example, a user may depress button 320 to begin the bolus event. Alternatively, the bolus event may be triggered by a preprogrammed algorithm within the electronics of system 100 or a handheld controller 1200 discussed below. Moreover, the bolus event may be selectively triggered by a user via the handheld controller 1200. Once the bolus event is triggered, the electronics within system 100 may cause batteries 710 to power one or both of electromagnetic coils 560. Once energized, these coils may attract one or both of magnets 580, which in turn will distort membrane 570, resulting in a volumetric change within the pumping chamber 524. This will allow medicament to flow from one or both of reservoirs 600, 610, into fluid receiving opening 521, through fluid channels 523a, 523b, and 523c, out of fluid discharge opening 524, and through one or both of inlet/outlet members 540, 540 into catheter 620. As a result of such operation, those of ordinary skill will recognize that medicament may be selectively delivered from one or both of reservoirs 600, 610.

Figure 11:
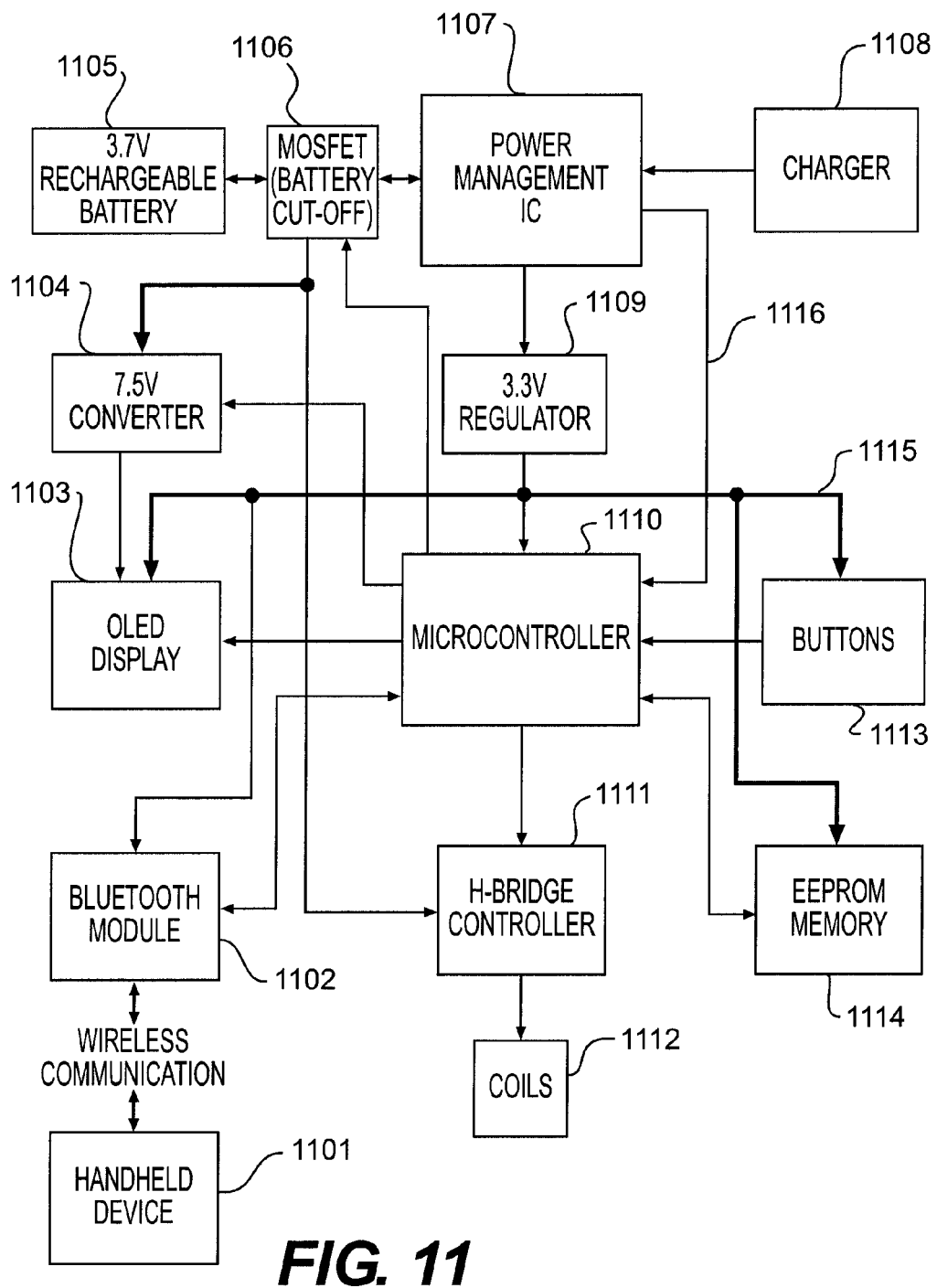
FIG. 11 is a schematic illustration of an exemplary power management system, in accordance with an embodiment of the present disclosure.

Referring to FIG. 11, major components of an exemplary system, such as, e.g., system 100, and their relative interactions are schematically illustrated. Although a different descriptive numeral may be used, the schematically illustrated components may correspond to one or more components of system 100 described above. The system 100 may include, but it not limited to, a microcontroller 1110, an H-bridge controller 1111, a plurality of electromagnet coils 1112, an EEPROM memory module 1114, an OLED display 1103, buttons 1115, an 7.5V converter 1104, a 3.7V rechargeable battery 1105, a MOSFET (battery cut-off) 1106, a Power Management integrated circuit (IC) 1107, a charger 1108, a 3.3V regulator 1109, and a Bluetooth module 1102 which may facilitate communication with a handheld module 1101. One or more of these various components may be operably coupled to one another by power lines 1115 and/or communication lines 1116.

The rechargeable battery 1105 supplies power for the electrical items of the exemplary system 100. In the powered state, a MOSFET (battery cut-off) 1106 transistor may be in the conduction state and allows current to flow from the battery to the connected devices. From the MOSFET 1106, power may be distributed to an H-bridge controller 1111, a 7.5V converter 1104 used to supply the appropriate voltage to the OLED display 1103, and the power management IC 1107, which, through the 3.3V regulator 1109, supplies power to all remaining components. Once powered, the microcontroller 1110 may begin executing code which coordinates the functions and timing of all other components. The buttons provide a means for direct user input to the exemplary system 100, while the OLED display 1103 provides a graphical display of data and information to be viewed by the patient.

The EEPROM 1114 serves as a non-volatile data retention memory module. The EEPROM 1114 and the microcontroller 1110 may be linked through a bidirectional communication path which allows the microcontroller 1110 to store and receive data at its discretion. While the contemplated embodiment illustrates EEPROM 1114 to be disposed within the housings 200, 210, any suitable remote memory storage may be used with the principles of the present disclosure.

The Bluetooth module 1102 allows for wireless communication between the system 100 and another Bluetooth enabled device such as a handheld controller, cellular phone, or personal computer. When pump operation is necessary, the microcontroller 1110 sends the appropriate signals to the H-bridge 1111 which activate the electromagnetic coils 1112 to drive the pump. When a charger 1108 is connected to the system 100, power flows into the power management IC 1107 which ultimately allows for recharging of the battery 1105.

As explained above, a battery 1105 (e.g., a lithium-ion battery), which is described above as battery 710, of system 100 may be charged and discharged through a Power Management Integrated Circuit (IC) 1207. The IC 1107 may be configured to regulate the current going in and out of the battery, monitor the temperature of the cell, and detect if a charger 1108 is connected. When a charger 1108 is present, the system may be powered from the charger 1108 and the battery 1105 may be charged at the same time. This IC 1107 may be a stand-alone controller and only reports its status to the microcontroller 1110. The power MOSFET 1106 controlled by the microcontroller 1110 may be connected directly to the battery 1105 to minimize power losses during storage. The battery 1105 or, if present, the charger powers the 3.3V output regulator 1109 that feeds all the electronic components of the system 100. The 7.5V output converter 1104 may be used to power an OLED display, such as, e.g., screen 300. The converter 1104 and the Bridge 1111 that control the coils 1112 are connected directly to the output of the power MOSFET 1106.

Figure 12:
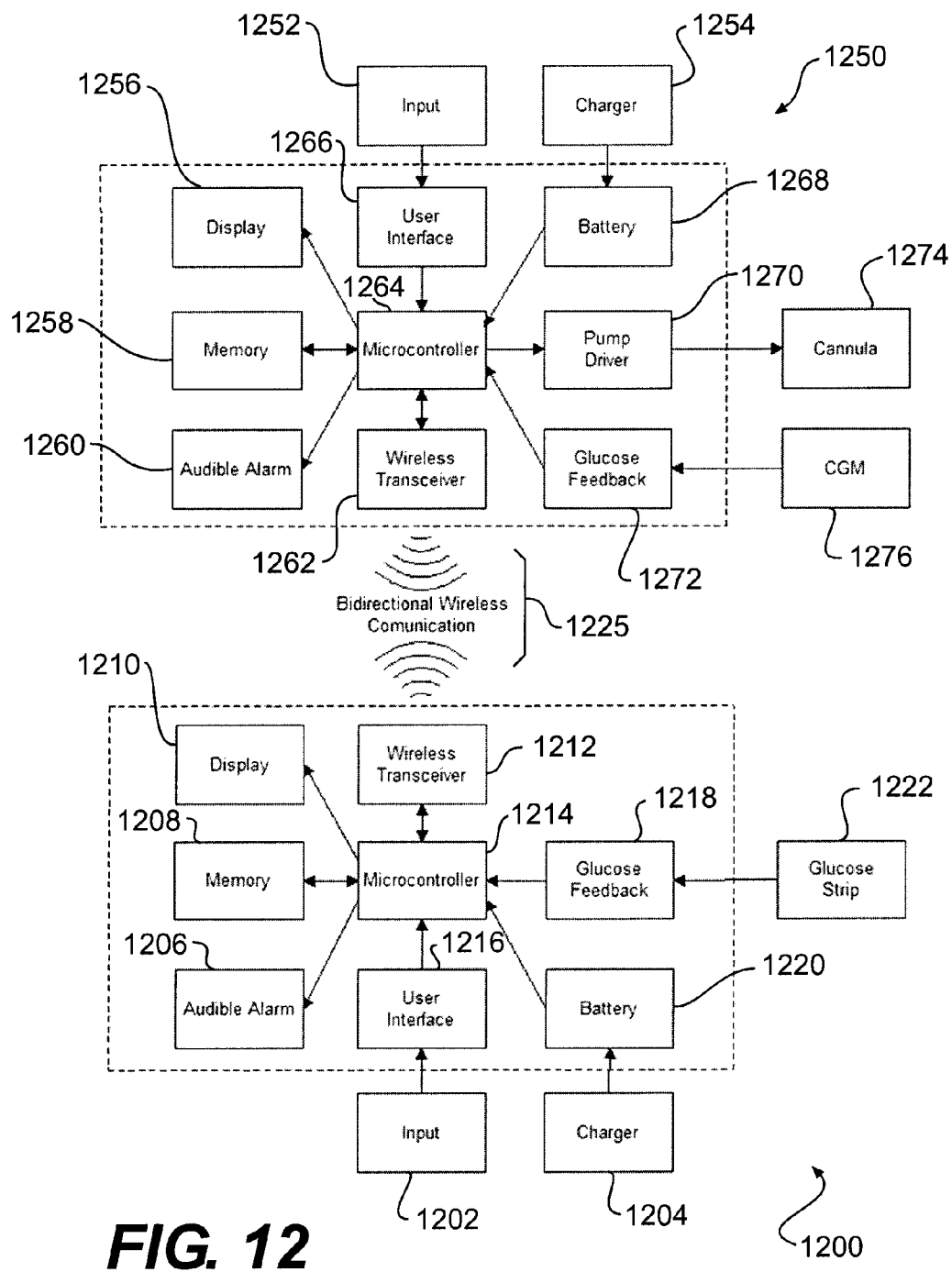
FIG. 12 is a schematic illustration of an exemplary miniature medicament delivery and continuous monitoring system in wireless communication with a controller.

Referring now to FIG. 12, an exemplary wireless micropump system, such as, e.g., system 100, and method of communication of the present disclosure are shown. Although different descriptive numerals may be used, the schematically illustrated components may correspond to one or more components of system 100 described above. After power up, the microcontroller 1264 may collect data from the EEPROM memory 1258 and display initial information on the screen of display 1256. The microcontroller 1264 may be constantly monitoring the time, the position of the buttons, and status of the battery 1268. The screen of display 1256 and an audible alarm and/or speaker 1260 may give important information and alert the user. The coils of pump driver 1270 of the pump may be powered through an H-bridge. The data collected by the device can be downloaded to the handheld controller 1200 or to a computer using a Bluetooth wireless connection (or any other suitable wireless communication means) via a suitable wireless transceiver 1272.

The handheld controller 1200 may be any suitable controller known in the art. In some embodiments, the handheld controller 1200 may include a display 1210, a wireless transceiver 1212, a memory 1208, an audible alarm 1206, a microcontroller 1214, a user interface 1216, one or more mechanisms for inputting data 1202, a glucose feedback algorithm module 1218, and battery 1220. In some embodiments, battery 1220 may be recharged by a charger 1204. In addition, controller 1200 may be configured to receive and analyze a blood sample on a glucose test strip 1222, as desired by the patient. The analysis of the blood sample on glucose test strip 1222 may be used to instruct system 100 to deliver a bolus dose and/or adjust the delivery of basal dosages of, e.g., insulin. Furthermore, one or both of system 100 and controller 1200 may be capable of wirelessly transmitting data to a computer server associated with a health care provider. In this manner, a health care provider may receive periodic updates regarding a user's glucose history and drug delivery characteristics.

In addition to, or independent thereof, system 100 may be configured to receive and analyze blood samples using a built-in continuous blood glucose (CGM) sensor 1276. The data received from the CGM 1276 may be used to instruct system 100 to deliver a bolus dose and/or adjust the delivery of basal dosages of, e.g., insulin. During a drug delivery event, the energized coils of pump driver 1270 result in a flow of medicament from the reservoirs 600 and/or 610 to the pump outlets and is ultimately delivered to the patient through a cannula 1274.

Figure 13:
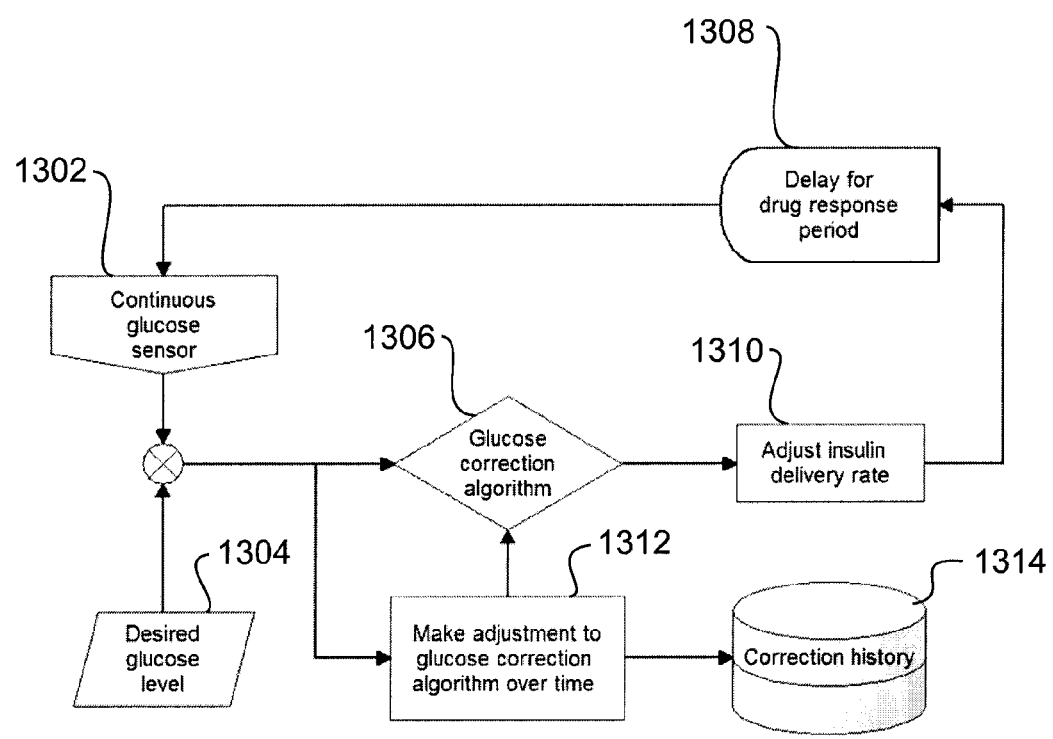
FIG. 13 is a schematic illustration of a body parameter feedback control based on continuous sampling of that body parameter.

Referring now to FIG. 13, there is a flowchart illustrating the operation principles of the embodiments disclosed herein based on glucose feedback control using continuous sampling. A Continuous Glucose Monitor (CGM) having a sensor 1302 may be constantly sampling the glucose level in a patient's blood stream and comparing it to a desired (e.g., a predetermined threshold) glucose level 1304. If the sampled level of glucose is higher than the desired glucose level 1304, an algorithm of the microcontroller may calculate the insulin dose the patient needs and adjust the insulin rate of delivery, step 1310, based on, e.g., glucose correction history 1314. The correction history 1314 may be also used to correct (step 1312) the glucose correction algorithm 1306. The modified glucose algorithm may take effect immediately to attempt to correct any observed imbalance in the patient and adjust the insulin delivery rate accordingly 1310. Following this alteration, a delay for drug response period 1308 may be introduced to allow the drug to act on the patient before resampling.

Figure 14:
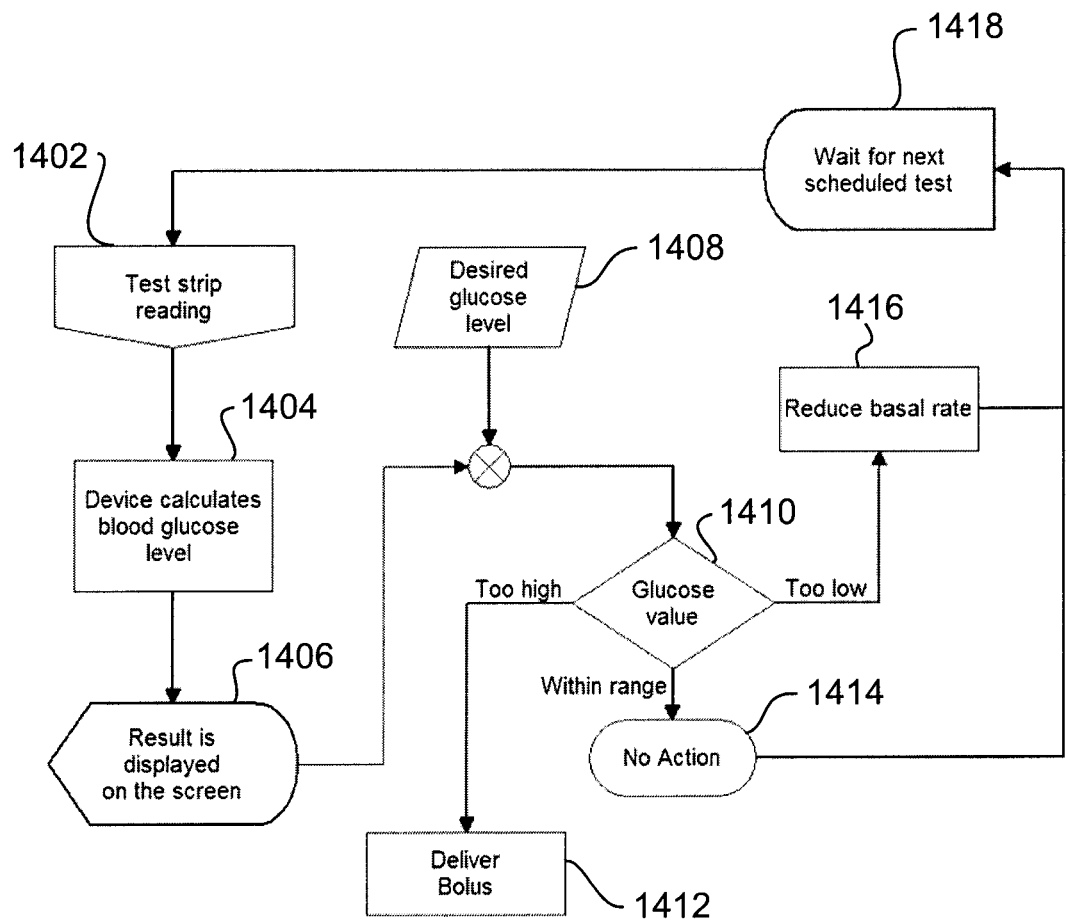
FIG. 14 is a schematic illustration of a body parameter feedback control based on period sampling of that body parameter.

Referring now to FIG. 14, the glucose feedback control using discrete test strips is described. A user of system 100 may be prompted to take a test strip reading at schedule interval, step 1418. To do so, the user may place a sample of blood on a conventional glucose test strip (not shown) and insert it into a suitable sensor module (not shown) provided on either system 100 or handheld controller 1200, step 1402. Regardless of where the sensor module is located, the device may then calculate the user's blood glucose level based on the blood sample, step 1404. The results of the test strip reading may be displayed on screen 310 of system 100 and/or on a screen (not shown) of controller 1200. An algorithm may then compare the results of the test strip reading to a desired glucose level 1408. If the test strip reading is within range of the desired glucose level 1408, then no action may be taken, step 1414. If the reading is too high, however, the system 100 may be triggered to deliver a bolus dose 1412. If, however, the test strip reading indicates that the user's blood glucose level is relatively low, the system 100 may be automatically adjusted to reduce the delivery rate of the basal dose, step 1416. Regardless of action taken, the controller 1200 or system 100 may prompt the user to take another test strip reading at the next predetermined interval, step 1418.

In some embodiments, it is contemplated may include additional optional features. Such features may include, but are not limited to, circuitry relating to fitness and/or a user's lifestyle. For example, system may include an integrated pedometer, a global positioning system (GPS), a music player, and so forth.

In accordance with the principles of the present disclosure, a method of using the disclosed embodiments will now be described. A user, such as, e.g., a diabetic patient, may be provided with a system 100. The user may remove a protective covering (not shown) from adhesive patch platform 240 and affix system 100 to a suitable skin location. Such a location may be, e.g., the user's abdominal area. If system 100 includes an integrated continuous glucose monitoring module 130, a cannula 420 may be also inserted into the patient's skin. Next, the user may use a handheld controller 1200 to activate and program the system 100 to delivery both basal and bolus doses of, e.g., insulin. Once the insulin from within reservoirs 600, 610 is depleted, the user may remove the original medicament cartridge 120 and replace it. If a suitable replacement is not available, however, the user may refill the reservoirs 600, 610. Further, if the continuous glucose monitoring module 130 becomes defective, the user may remove module 130 and replace it as desired. In addition, the user may verify the results of the continuous glucose monitoring module 130 may analyzing blood samples via a test strip sensor on controller 1200.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

What is claimed is:

1. A miniature medication delivery system for delivery of medicament to a body of a user, comprising:

a housing configured to be secured proximate to the body, the housing comprising control electronics, a power source, a plurality of electromagnetic coils, and a sensor support socket;

a first sensor configured to continuously monitor a parameter of the user removably connectable through the sensor support socket, wherein the first sensor is configured to be inserted into the body of the user through the sensor support socket;

a cartridge system removably connectable to the housing comprising:

a first reservoir comprising a first medicament;

a second reservoir comprising a second medicament; and a pump mechanism configured to pump medicament from the first reservoir to a delivery mechanism having a portion disposable within the body of the user, wherein the control electronics are in electrical communication with the first sensor, the pump mechanism comprising:

a first pump insert body in fluid communication with the first reservoir, wherein the first pump insert body comprises a first opening that contains a first magnet, a plurality of fluid channels, a fluid receiving opening, and a fluid discharge opening;

a second pump insert body in fluid communication with the second reservoir, wherein the second pump insert body comprises a second opening that contains a second magnet;

a flexible member disposed in between the first and second pump insert bodies, wherein the flexible member is operably coupled to first and second magnets, wherein the plurality of electromagnetic coils are configured to selectively control position of one or both of the first and second magnets relative to the plurality of electromagnetic coils in order to deliver the first and the second medicament.

2. The miniature medication delivery system of claim 1, wherein the first medicament comprises a fast-acting insulin, and the second medicament comprises a slow-acting insulin.

3. The miniature medication delivery system of claim 1, wherein the parameter is blood glucose.

4. The miniature medication delivery system of claim 1, wherein the first sensor comprises a cannula configured to be disposed within a user's blood stream.

5. The miniature medication delivery system of claim 1, wherein the cartridge system is disposable.

6. The miniature medication delivery system of claim 1, wherein the housing further includes a display screen.

7. The miniature medication delivery system of claim 1, wherein the delivery mechanism includes an infusion set having a catheter.

8. The miniature medication delivery system of claim 1, wherein the pump mechanism is configured to pump the first medicament at a first rate of delivery and the second medicament at a second rate of delivery.

9. The miniature medication delivery system of claim 1, wherein the housing includes a plurality of surfaces, and at least one of the plurality of surfaces includes an adhesive material thereon.

10. The miniature medication delivery system of claim 1, wherein the first medicament is different from the second medicament.

11. The medication delivery system of claim 1, wherein the housing includes a height of approximately 0.5 inches.

12. The miniature medication delivery system of 1, wherein the parameter is glucose.

13. The miniature medical delivery device of claim 1, wherein one or both the first reservoir and the second reservoir are refillable.

14. The miniature medical delivery device of claim 13, wherein a release of one or both the first medicament and the second medicament occurs automatically based on receiving parameter data outside of a predefined threshold range of the parameter.

15. The miniature medical delivery device of claim 1, wherein a release of one or both the first medicament and the second medicament occurs when the control electronics receives a release prompt.

16. The miniature medical delivery device of claim 1, wherein a parameter level is periodically transmitted to an external device.

17. The miniature medical delivery device of claim 1, wherein a dosage quantity of one or both the first medicament and the second medicament is determined based on receiving parameter data outside of a predefined threshold range of the parameter.

18. The miniature medical delivery device of claim 1, wherein the power source is rechargeable.

* * * * *